US011266353B2

(12) United States Patent
Massak et al.

(10) Patent No.: US 11,266,353 B2
(45) Date of Patent: Mar. 8, 2022

(54) SUPPORT SYSTEM AND METHOD

(71) Applicant: AERGO LTD, London (GB)

(72) Inventors: Christoph Massak, Sierning (AT);
Daniel Garrett, London (GB);
Hsin-Hua Yu, London (GB)

(*) Notice: Subject to any disclaimer, the term of this patent is extended or adjusted under 35 U.S.C. 154(b) by 337 days.

(21) Appl. No.: 15/750,923

(22) PCT Filed: Aug. 8, 2016

(86) PCT No.: PCT/GB2016/052468
§ 371 (c)(1),
(2) Date: Feb. 7, 2018

(87) PCT Pub. No.: WO2017/025735
PCT Pub. Date: Feb. 16, 2017

(65) Prior Publication Data
US 2018/0228441 A1 Aug. 16, 2018

(30) Foreign Application Priority Data
Aug. 7, 2015 (GB) .................... 1513967

(51) Int. Cl.
A61B 5/00 (2006.01)
A61G 7/057 (2006.01)
A61G 5/10 (2006.01)

(52) U.S. Cl.
CPC .......... *A61B 5/6894* (2013.01); *A61G 5/1043* (2013.01); *A61G 5/1048* (2016.11);
(Continued)

(58) Field of Classification Search
CPC .. A61B 5/6894; A61G 5/1048; A61G 5/1091; A61G 5/1043; A61G 7/05769; A61G 2203/12; A61G 2203/34; A47C 7/02; A47C 7/16; A47C 7/20; A47C 7/85; A47C 7/425
See application file for complete search history.

(56) References Cited

U.S. PATENT DOCUMENTS 4,753,482 A * 6/1988 Warren .................... A61G 5/00
297/284.1
5,121,938 A * 6/1992 Gross .................... A47C 31/11
280/304.1
(Continued)

FOREIGN PATENT DOCUMENTS

CA 1159582 A * 12/1983 ............. A47C 7/405
DE 102005011738 A1 * 11/2006 ............... A61G 5/12
WO WO-2010076781 A2 * 7/2010 ............... A47C 7/46

*Primary Examiner* — David R Hare
*Assistant Examiner* — Alexis Felix Lopez
(74) *Attorney, Agent, or Firm* — Lightfoot & Alford PLLC

(57) ABSTRACT

A posture support system for a person supporting appliance comprising: a module (300), each module (300) comprising: an expandable body (20), means (60) for changing the degree of expansion of the expandable body (20); a sensor (27) configured to produce measurement data corresponding to the degree of expansion of the expandable body (2); a processor (116) arranged to process the measurement data generated from the sensor (27); and a wireless communication unit (114) arranged to transmit the measurement data wirelessly to a controller (320) and receive control data to control the degree of expansion of the expandable body (20).

13 Claims, 12 Drawing Sheets

(52) U.S. Cl.
CPC ........ *A61G 5/1091* (2016.11); *A61G 7/05769* (2013.01); *A61G 2203/12* (2013.01); *A61G 2203/34* (2013.01)

(56) References Cited

U.S. PATENT DOCUMENTS

| | | | | |
|---|---|---|---|---|
| 5,211,446 A * | 5/1993 | Jay | ............................ | A61G 5/12 297/284.7 |
| 6,312,051 B1 * | 11/2001 | Adams | ................. | A47C 31/113 297/228.11 |
| 7,441,294 B2 * | 10/2008 | Mossbeck | ............ | A47C 27/082 297/452.41 |
| 2004/0193078 A1 * | 9/2004 | Flick | .................... | A61H 9/0078 601/58 |
| 2005/0116525 A1 * | 6/2005 | Holcomb | ............. | A61G 5/1054 297/452.29 |
| 2008/0122267 A1 * | 5/2008 | Larson | ................... | A47C 7/021 297/4 |
| 2009/0093912 A1 * | 4/2009 | Wilker, Jr. | ............. | A61G 7/052 700/282 |
| 2010/0225489 A1 * | 9/2010 | Hinterlong | ......... | G08B 21/0461 340/573.4 |
| 2011/0213503 A1 * | 9/2011 | Porter, III | .......... | A61G 7/05769 700/282 |
| 2012/0065560 A1 * | 3/2012 | Siegner | .............. | A61G 7/05776 601/150 |
| 2013/0019408 A1 * | 1/2013 | Jacofsky | ................ | G16H 40/63 5/613 |
| 2013/0255699 A1 * | 10/2013 | Squitieri | ................. | A61F 5/34 128/892 |
| 2015/0351981 A1 * | 12/2015 | Sazonov | ................... | G01L 5/00 297/217.2 |
| 2016/0022520 A1 * | 1/2016 | Streeter | ................ | A61G 5/1043 5/655.3 |

* cited by examiner

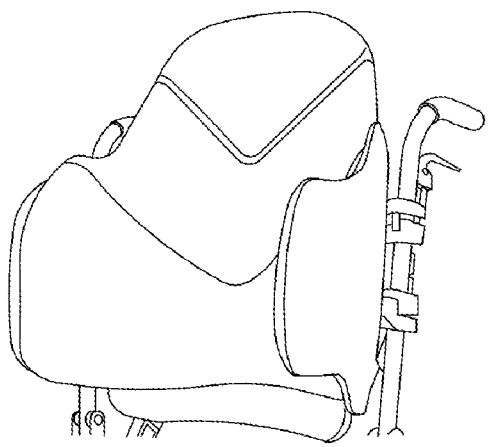
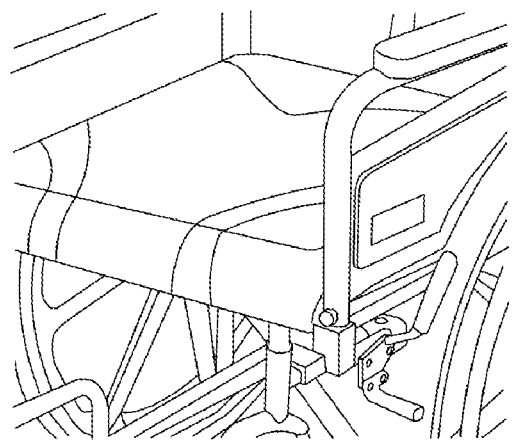
Figure 23          Figure 24
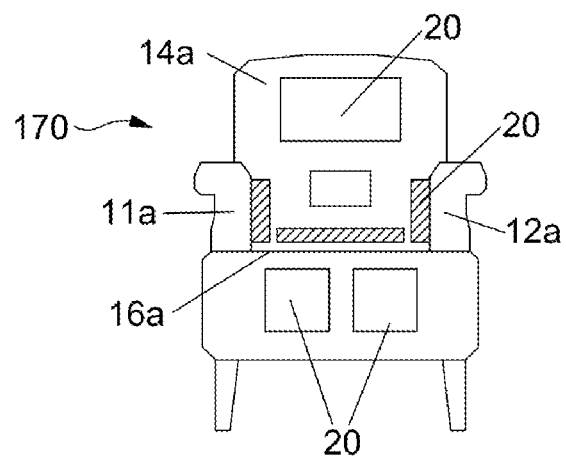
Figure 26

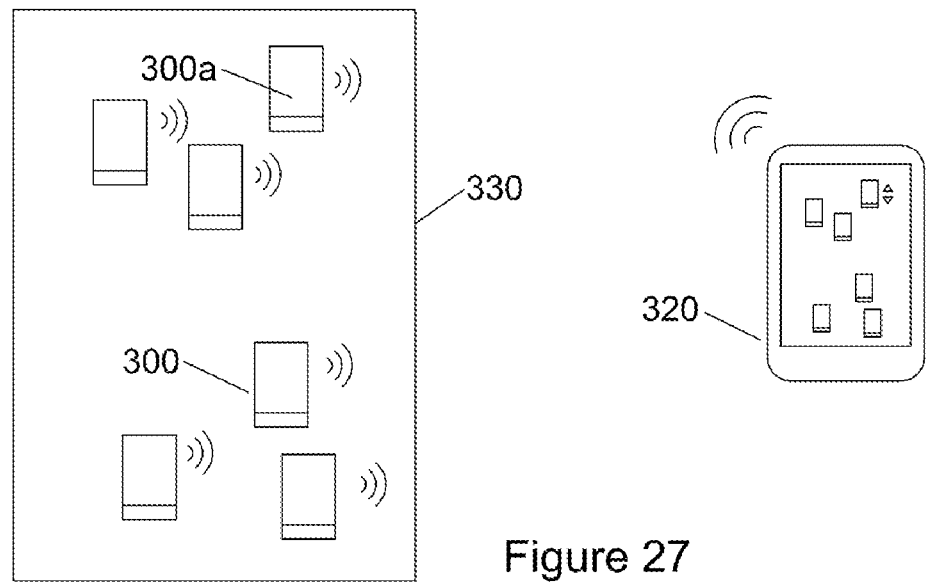
Figure 27
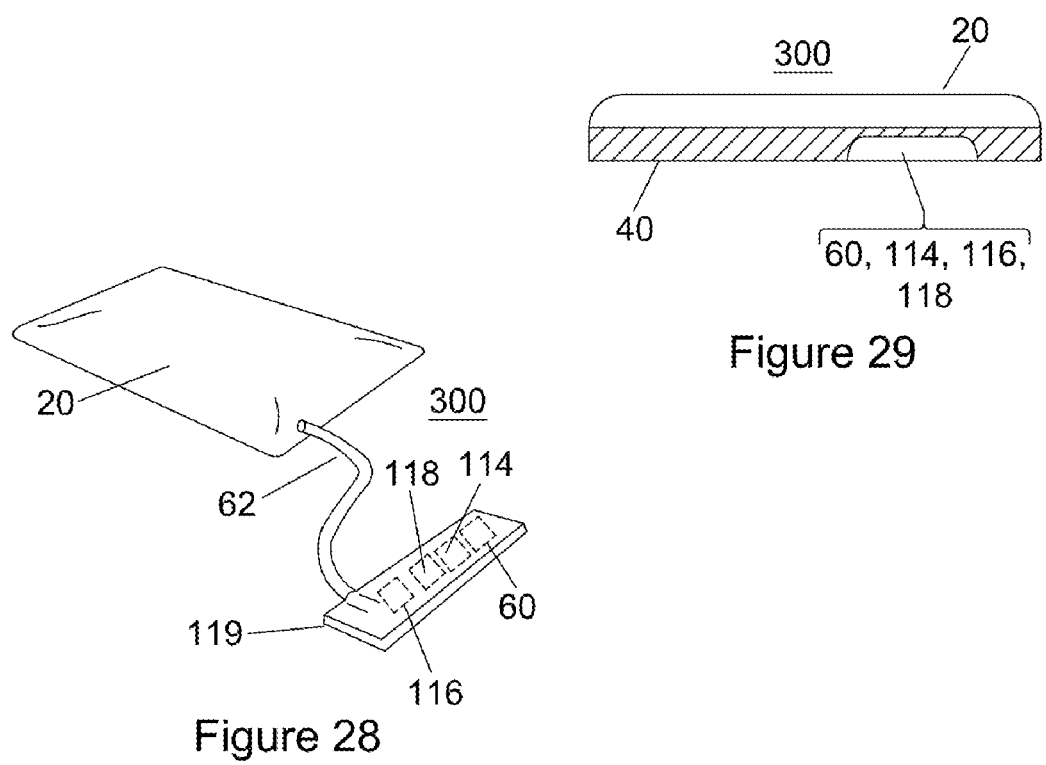
Figure 29
Figure 28

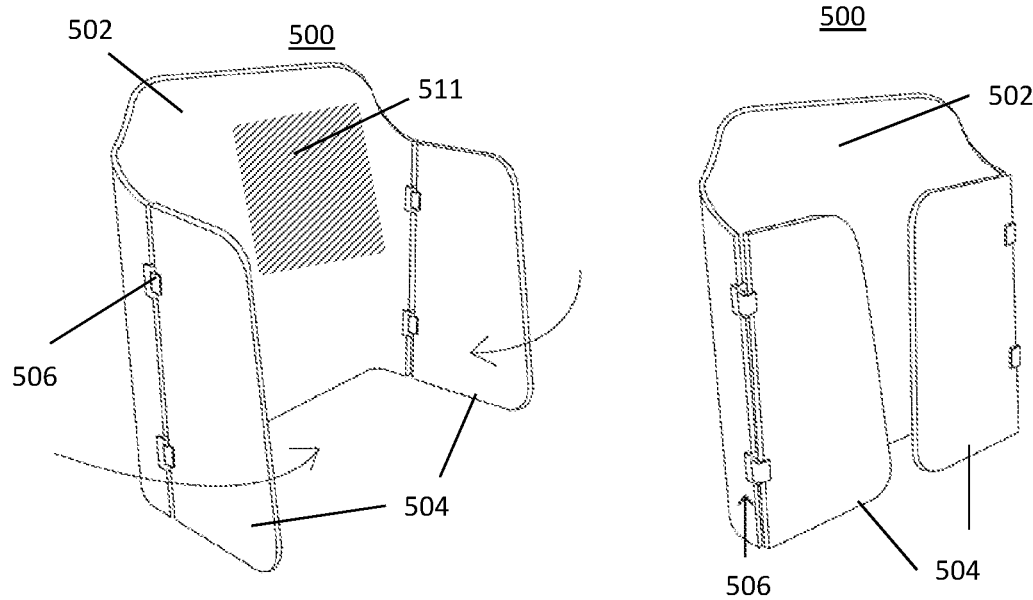
Figure 30
Figure 31
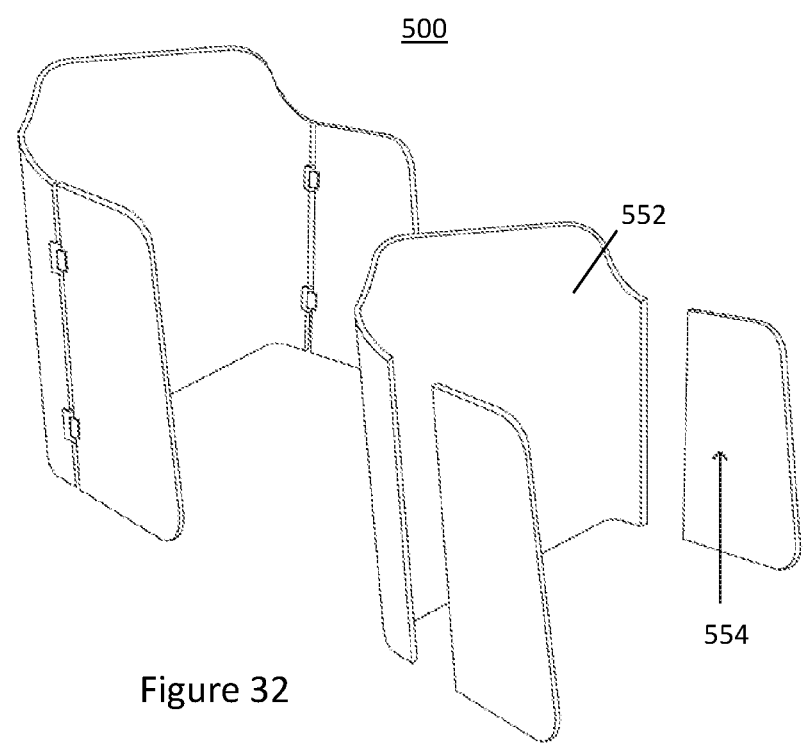
Figure 32

SUPPORT SYSTEM AND METHOD

This invention relates to a support system, in a particular a posture support system. Such a system is adapted to be fitted to, or used with, a wheelchair or other person supporting appliance. The invention also relates to various methods, in particular a method of fitting the posture support system to a wheelchair or other person supporting appliance, a method of monitoring the posture support system and a method of controlling the posture support system.

BACKGROUND

Many wheelchairs users suffer from a muscular and/or skeletal disability that leads to postural difficulties. For example, a person may slump in a wheelchair and in particular they may slump to one side. The posture of a wheelchair user can have significant physiological, psychological and social implications.

Examples of disabilities that lead to postural difficulties include muscular dystrophy and cerebral palsy. About 1 in 500 children in the UK have cerebral palsy. Scoliosis is a fairly common medical condition that also causes postural difficulties. Scoliosis often accompanies other medical conditions; such "secondary" scoliosis can be the result of a neuromuscular condition (e.g., spinabifida, cerebral palsy or spinal muscular atrophy), a physical trauma or a syndrome. In the UK there are approximately 1.2 million wheelchair users and up to about 70% of people over 65 have scoliosis. One in 250 children has scoliosis. As such, there is an ongoing and significant need for wheelchair systems that can correct, or compensate for, a person's posture, for example, to maintain a person in a relatively upright/vertical position.

A correct posture is important for both medical and social reasons. For example, it is important that a person's torso is aligned above their hips so as to mitigate digestive problems. In another example, poor positioning of a person's head may increase the risk of aspiration (in which food or liquid enters the person's lungs) potentially causing pneumonia. Pneumonia is particularly dangerous and life threatening for wheelchair uses who have an underlying primary medical condition.

Poor posture can often make a disabled person appear more disabled than they actually are. This can cause the disabled person to be treated inappropriately or be stigmatised. For example, poor posture may give a false impression that the disabled person has learning difficulties in addition to physical disabilities or that the person has learning difficulties that are greater than they actually are.

A well-known adjustable wheelchair system is the Matrix system, a portion of which is illustrated in FIG. 1. The matrix system typically comprises an array of adjustment points that are connected by four rotatable ball joints. Each joint can be adjusted by means of a tool such as an Allen key. Such a system provides a very large number of different configurations that can be achieved so that the support provided to a wheelchair user by the system is highly customizable. Matrix systems are highly engineered. They are relatively expensive and can cost in the region of several thousand pounds sterling or several thousand US dollars.

A problem with such systems is that they can require several hours to obtain an appropriate customised adjustment. The adjustment usually requires an experienced physiotherapist and/or occupational therapist or suitably qualified clinician. The adjustment process can be complex and it is not uncommon for there to be more than one therapist, clinician and/or technician involved with a particular adjustment process with each participant bringing their own experience, knowledge and skills to bear on the adjustment process.

Often, it is required for the wheelchair user to be hoisted out of the wheelchair whilst the wheelchair is being adjusted and then hoisted back into the wheelchair to check the fit and support provide of the new adjustment. Often various covers and padding need to be removed in order to enable an adjustment to be made. This process may need to be repeated many times with the aim of improving the fit and the support provided by the system with feedback being provided by the user and/or the user's carer or support worker. It can be that the wheelchair is adjusted during a lengthy appointment only for the adjustment to be found unsuitable for the wheelchair user in the hours, days and weeks following the visit. Furthermore, a wheelchair user's physiology may change in the short, medium and/or long term, with the changes requiring repeat visits for further assessment or adjustment.

Some posture correction systems that are currently on the market use foam wedges and metal structures to hold a wheelchair user in a particular position. In common with Matrix systems, adjustment of such systems can be time consuming and cause distress to the wheelchair user. This is particularly the case if the wheelchair user requires physical handling and/or then requires to be winched in and out of the wheelchair so that adjustments can be made to the wheelchair system. Such winching often needs to be performed several times in order to determine an appropriate wheelchair configuration. The adjustment of such known systems can be particularly distressing, embarrassing and/or dehumanising. This can be particularly the case for young people, for example, young people in the age range 10 to 18 years old. Like anyone else, wheelchair users do not like to be manhandled by people that are strangers to them. Adolescents can be particularly sensitive to being handled by someone else, even a known physiotherapist or occupational therapist.

Existing solutions for wheelchair adjustment are often bulky, expensive and unsightly and can have a negative effect on the wheelchair user's self-esteem. Such systems can make a wheelchair users feel alienated from other people and make them self-conscious. Such systems are a barrier to socialisation.

A commercially available postural support system is provided by Summarise Medical with their "Jay Back" system that uses a system of Velcro® and wedges.

U.S. 2006/192362A describes a pneumatic support system for a wheelchair that uses an inflatable support unit. The system includes a control unit that permits a user to control whether the support unit gets inflated or deflated and also includes a pressure sensor system that defends against over inflation of the air bladders. The pressure sensors provide pressure readings of each air bladder so as to allow continuous bladder pressure monitoring.

Several prior art systems comprises a multitude of air cells arranged in a matrix formation. U.S. 2006/085919A describes a person support surface comprising a multitude of inflatable cells and a driver associated with each of the inflatable cells so that each driver may be operated to individually inflate the corresponding inflatable cell. A master controller may be used to control the overall contour of the person support surface and control the overall pressure profile via operation of the drivers. U.S. 2006/168734A describes a cellular support cushion in which each cell is an inflatable bag that can be repeatedly filled and depleted. U.S. 2004/422611A describes a plurality of matrices of air support cells that can be individually inflated and deflated. A remote control device can be used for controlling the inflation/deflation. U.S. 2014/026327A describes an adaptive cushion for reducing pressure on body parts of a person positioned on a chair or bed. The cushion includes a controllable inflating and deflating matrix of individual air bladder cells.

U.S. Pat. No. 7,059,678B describes a portable orthopaedic support device that includes individual inflatable independent body and torso supports and chambers for legs, lumbar, shoulder blade and neck areas. A combination of an air pump and a selector valve is provided for selective delivery of compressed air through a conduit assembly to each of the inflatable supports. U.S. 2012/090698A describes a pressure control and feedback system for an adjustable foam support that includes a vacuum pump for drawing air from a hermetically sealed foam core to reduce the firmness of the core. US5662384A describes a seating cushion system which provides alternating support regions by dynamic inflation of a set of cells. Japanese application JP60174334A describes a rear seat containing airbags and a posture detecting device that can automatically detect a seating posture and adjust the seat accordingly. Chinese patent application CN104323911A describes a multi-functional smart cushion in which cushion force data is measured and transmitted to a central processor for processing so that the need to adjust the sitting position can be determined.

SUMMARY

Aspects and embodiments of the invention are set out according to the appended claims.

A first aspect of the invention provides a posture support system for a person supporting appliance comprising: one or more modules (in an exemplary embodiment, a plurality of modules), each module comprising: an expandable body, means for changing the degree of expansion of the expandable body; a sensor configured to produce measurement data corresponding to the degree of expansion of the expandable body; a processor arranged to process the measurement data generated from the sensor; and a wireless communication unit arranged to transmit the measurement data wirelessly to a controller and receive control data from the controller to control the degree of expansion of the expandable body.

Since each module has its own means for changing the degree of expansion of the expandable body, there is no need for there to be a physical connection (e.g. conduits and/or wires) between the modules and another unit or between the modules themselves. Since the modules are unfettered by physical connections there is a large degree of freedom as to how they can be attached to a posture support system. The lack of physical connections also makes it easier for a person to attach the modules and/or adjust the position of the modules on the posture support.

A modular system is advantageous since it is easier to repair, replace or service individual modules than it is for a connected system. For example a single module, or a subset of modules used in a modular system could be sent away for repair or servicing and the modules that are sent away could be replaced by spare modules (or the remaining modules could be reconfigured to account for the missing module(s)).

In one embodiment, the expandable body is an inflatable bladder and the means for changing the degree of expansion of the inflatable bladder is a source of compressed gas such as a pump. Rather than having a single pump that supplies compressed air to all of the bladders, each module has its own individual pump that supplies air to the bladder of that module. The individual pumps can be smaller and less powerful than if a single pump where used. A user of the person supporting appliance, in particular a person who has learning difficulties (or otherwise has reduced cognition), may become distressed by a noisy pump. A plurality of less powerful pumps is advantageous compared to the use of a single large pump, when only a subset of the plurality of pumps is use because they will generally be quieter.

In an embodiment of the invention, the system of comprises a support structure to which the module or each module is attached or are adapted to be attached. Generally, the support structure is rigid so that it can support a person.

The support structure may be an upper body support system that comprises at least one lateral support portion connected to, and extending from, a lateral side of the back support portion, wherein the lateral support is adapted to pivot about the lateral side of the back support. For example, the at least one lateral portion is adapted to pivot between a deployed position in which the at least one lateral portion extends outwardly from the back support portion and a stowed position in which the at least one lateral portion extends inwardly with respect to the back support portion A second aspect of the invention provides a posture support assembly for a wheelchair comprising: an attachment surface; and an expandable body having an attachment arranged to attach to the attachment surface so as to provide a degree of freedom for the position of the expandable body on the attachment surface and a degree of freedom in the extent of expansion of the expandable body.

This aspect of the invention is in contrast to prior art systems that use wedges. In such systems once a wedge has been placed it cannot be adjusted without reconfiguration of the wedge.

Rather than having a matrix of airbags that can be individual inflated to provide support over a particular area, the current invention provides an expandable body which can be moved to a required position to support a wheelchair user sat in the wheelchair. For example, the expandable body can be placed anywhere on a back portion or thoracic portion of a wheelchair. This provides an elegant solution that transcends the needs for complicated over engineered solutions. The invention allows a system that can be scalable produced such that the assembly can be mass produced. This reduces production costs and makes the assembly more affordable than prior art support systems. In addition, the same individual posture support assembly can be used for different users of the same wheelchair or for different wheelchairs, including wheelchairs of different design/construction.

The expandable body may take the form of an airbag but it may take other forms. For example, the expandable body may comprise self-inflating foam or material that changes its dimensions in response to an electrical signal (e.g., an electro-restrictive or magneto-restrictive material). More than one expandable body can be used on a wheelchair or wheelchair component. As one particular example, a thoracic support component of a wheelchair may have an expandable body placed on either side of the support component to support the different sides of a wheelchair user.

In an embodiment, the attachment surface and the expandable body each comprise releasably engageable material. The attachment surface and the attachment together may form a hook and loop attachment system, for example, the attachment surface and the attachment may each comprises an area of Velcro®.

A third aspect of the invention provides a posture support system for a wheelchair comprising: one or more expandable bodies, each having a connection to connect the, or each, expandable body to the wheelchair; one or more sensors arranged to measure the pressure within an expandable body (for example the internal pressure of an air bag) and/or the pressure exerted by the expandable body on another surface; a processor arranged to receive measurement data generated from the one or more sensors; and a memory arranged to store measurement data from the one or more sensors and/or store processed data produced by the processor.

The processed data may comprise a historical record of the level of pressure applied by the, or each, one or more expandable bodies to a wheelchair user occupying the wheelchair. The historical record allows a health care professional or practitioner such as, for example, a physiotherapist or occupational therapist, to assess the support regime or protocol being used to support an individual. The information may also be of use to a wheelchair technician qualified to adjust wheelchairs. The historical data can, therefore, guide the care of a patient or assist a healthcare practitioner in the performance of a procedure such as making one or more adjustments to the wheelchair and/or posture support system.

The measurement data and/or processed data, may be accessed by connecting an electronic storage device to the an output port of the system, for example a memory stick, dongle, CD/DVD writer or other media writer may be connected to the support system. Data transferred to such devices may be then be accessed, reviewed and/or processed at a remote location e.g. by a health professional.

In an embodiment, the posture support system comprises a display configured to display measurement data and/or processed data, for example the display may take the form of a graphical user interface (GUI). The GUI may be in wired or wireless connection, or a combination of both wired and wireless connection, with the rest of the system. The GUI may take the form of a mobile device such as a mobile phone, tablet, laptop, personal digital assistant (PDA) or the like. Such devices can be configured to access data from the rest of the system, analyse or further analyse that data, record data and/or communicated the data to other devices. For example, the data may be communicated to other devices via the Internet or other communication network (e.g., a mobile phone network or Bluetooth). In this way the data from a posture support system for a wheelchair may be transmitted and reviewed by a healthcare care professional or wheelchair technician in a remote location or by the wheelchair user themselves. For example, the healthcare professional may be, say, an occupational therapist based at a hospital or clinic some distance from the location of the wheelchair; or a wheelchair technician may be located at a manufacturing, design or customer service site or be travelling between clients. The GUI could also be used by an on-site professional to adjust the wheelchair user's posture without the need to manhandle the user.

Often it may take some time for a wheelchair user to have his or her wheelchair assessed. Assessment appointments are often only available several weeks, or even months in advance. The use of a data transmittal system may allow a wheelchair user to have his wheelchair assessed more promptly and without the need for the wheelchair user to make a visit to a healthcare professional and/or wheelchair technician. Such visits often present a number of issues such as the transportation needs of the wheelchair user and the medical needs and comfort of the wheelchair user during transportation and during the appointment. Such visits can also be stressful and have a psychological impact on the wheelchair user. Eliminating or reducing the need for such visits would be of great benefit to the wheelchair user and reduce the impact on transportation resources such as wheelchair accessible vehicles.

Human resources such as physiotherapists, occupational therapists or other health professionals are often limited and generally under budgetary constraint. Aspects and embodiments of the invention provide a technical tool that can alleviate this problem. For example, embodiments of the invention may allow an "in-house" therapist based at, say, a school, to be able to attend to the needs of a wheelchair user with fewer interventions. The interventions would also be shorter. For example, the interventions would take less time because the wheelchair user would not need to be hoisted or the number of times that hoisting was performed during an intervention would be reduced. In this way, the same number of therapists can provide support for a larger number of wheelchair users or provide improved care for the same number of wheelchair users.

In one scenario, the data obtained from the wheelchair support system can be remotely assessed by a health professional and an appointment made for the wheelchair user only if the data indicates that this would be beneficial. The health professional/therapist may also assess data from various wheelchairs and prioritise the need to adapt the wheelchairs in accordance with the data. By considering the data, the health professional/therapist can reduce the number of interventions, for example, the data may indicate that an intervention would produce no improvement, or only marginal improvement, in a wheelchair user's posture at the current time.

In an embodiment of the invention, the posture support system comprises a controller for controlling the degree of expansion of at least one of the one or more expandable bodies. In this way, configuration or control data may be sent to the controller to adjust the posture support system according to predefined values. For example, the degree of expansion may be controlled using a feedback signal from the one or more sensors so that measurements made by the one or more sensors matches values determined by the control data. The controller may be part of the graphical user interface device or respond to signals generated by such a device.

The posture support system may comprise a shape memory component covering the expandable body. For example, the shape memory component may comprise viscoelastic polyurethane foam.

A fourth aspect of the invention provides a posture support assembly for a wheelchair comprising: an attachment surface; an expandable body having an attachment arranged to attach to the attachment surface at a position that has two degrees of freedom on the attachment surface; and a shape memory material arranged to fit over the expandable body when the expandable body is attached to the attachment surface.

The use of a shape memory component allows for a better engagement between the support system and the wheelchair user since the one or more expandable body can provide a surface that is a better fit to the body of the wheelchair user.

A fifth aspect of the invention provides a cover to fit over a component of a wheelchair, wherein the component comprising the posture support assembly and the cover is configured to fit over the component when the expandable body is in an unexpanded/stowed form and remain fitted to the component when the expandable body is expanded/deployed form.

A sixth aspect of the invention provides a kit comprising the cover and a set of instructions, wherein the set of instructions comprises instructions to: fit the cover to the component when the expandable body is in stowed state; and expand the expandable body. The kit may also include the expandable body.

The cover is easy to fit since the unexpanded body is smaller than when it is in its expanded/deployed state. The same cover could be used if the wheelchair assembly needs to be adapted to account for changes to a wheelchair user's posture, or for growth of a young wheelchair user.

A smaller size cover can therefore be used than would otherwise be necessary when fitting a cover to a component. Hence a particular pre-defined size will fit a larger range of wheelchair sizes and wheelchairs that have adaptions for individual users. Covers can therefore be made that have a standardised size. This allows reduction in manufacturing costs and it becomes more feasible to produce a range of aesthetic designs.

The cover may have one or more access openings, such as one or more slits, that provide a user access an expandable body of the posture support system. For example, the cover can have an aperture that allows access for a person's fingers or hand so that the person may move the expandable body at a chosen position on the attachment surface. This allows the support provided to a wheelchair user to be adjusted whilst the wheelchair user remains in the wheelchair thereby reducing the amount of hoisting necessary in order to complete the adjustment process thereby reducing distress caused to the wheelchair user.

A seventh aspect of the invention provides a method of adjusting a wheelchair comprising the steps: (a) providing a support surface having an outward facing attachment surface; (b) placing an expandable body at a chosen position on the attachment surface; and (c) altering the degree of expansion of the expandable body and (d) fitting a cover to a wheelchair component, the wheelchair component having the attachment surface with the expandable body attached thereto. The order of the steps is not necessarily as that listed according to the seventh aspect of the invention—although they are in that order in an embodiment of the invention.

An eight aspect of the invention provides a method of monitoring a person's posture or position comprising: (i) receiving measurement data communicated by a posture support system fitted to a wheelchair whilst a user is seated in the chair; (ii) logging the measurement data; and (iii) analysing the measurement data to determine changes in posture of the user. The method may further comprise: (iv) generating adjustment data for adjusting the posture support system; and (v) communicating the adjustment data to the posture support system. The receiving step (i) and/or the generating step (iv) may be performed on a device that is remote from the wheelchair.

The adjustment data is at least partially derived from the logged measurement data received from the wheelchair and/or previously logged measurement data obtained from one or more other wheelchairs.

A ninth aspect of the invention provides a kit comprising: one or more inflatable bodies and instructions to fit the one or more bodies to an attachment surface A tenth aspect of the invention provides a method of treating a medical condition of a wheelchair user comprising: providing a posture support system comprising one or more expandable bodies; and generating signals to periodically adjust the degree of expansion of the one or more expandable bodies according to a predefined protocol.

The support system may be fitted to a thoracic support component of a wheelchair and the generated signals may cause the expandable bodies to cyclically expand and contract to cause the torso of the wheelchair user, when in the wheelchair, to move from side to side. The support system may also be fitted to the seat of the wheelchair for pelvic repositioning and/or the relief of pressure on the wheelchair user.

A eleventh aspect of the invention provides a kit comprising: one or more expandable bodies, wherein the, or each, expandable body comprises an attachment configured to releasably engage with an attachment surface at a position that has two degrees of freedom on the attachment surface; and instructions to fit the expandable bodies to the attachment surface. The instructions may comprise instructions for a person to engage the expanded body with the attachment surface at a desired location on the attachment surface. The kit may comprise: one or more pieces of attachment material to form one or more attachment surfaces, wherein the instructions include instructions to fit the attachment material to a support surface or other component of a wheelchair.

An embodiment of the invention comprises a rigid structure for use with the one or more expandable bodies. The expandable bodies can be attached to, embedded or otherwise connected or deployed from the rigid structure. The structure is rigid in that it exhibits negligible flexing when the one or more expandable bodies expand or contract. The expandable bodies may exert a pressure of up to 140 psi (10 kgs/cm$^2$) or in the case of the expandable bodies being bladders the internal pressure of the bladders may be up to 140 psi (10 kgs/cm$^2$).

The rigid structure may be fitted to a wheelchair, be an existing component of the wheelchair or replace a component of the wheelchair. In one example the rigid structure is the back for a wheelchair. The back may be placed on top of an existing back that is already part of the wheelchair or may replace a back system that is already in place. Instead of being a back support, the rigid structure can be configured to be, for example a seat, a lumbar support, a thoracic support, a head rest, a neck support or a component thereof. The use of a rigid structure in conjunction with an expandable body allows for more accurate posture control and monitoring. This is because the expansion of the expandable body will cause a proportional force or displacement to be applied to the person of the wheelchair user. If the expandable body were to be connected to a structure that was not rigid then part of the expansion of the expandable body would be taken up by flexing of the structure rather than movement of the user. Preferably, the rigid structure should be hard enough so that it does not compress when the expandable bodies expand.

Although aspects and embodiments of the invention relate to a posture support system for use with a wheelchair, the posture support system may also be used together with other appliances. For example, the system may be used with a bed. Often wheelchair users make use of other support means other than wheelchairs such as, for example, beanbags and specialised equipment such as side lying boards and standing frames. The posture support system of the current invention is highly adaptable so that it can be fitted to such equipment with little or no modification. This advantage is the result of the system being highly adjustable simply by moving the expandable body to the required position and adjusting the degree of expansion of the body to an appropriate level.

In aspects and embodiments of the invention the posture support system and methods are applied to a chair that is not a wheelchair or the support system is applied to some other static disability seating system. Such a chair/seating system is generally configured to be stationary whilst occupied by a user.

In one embodiment, the posture support system is used, or adapted to be used, in conjunction with a bed so that the position of an occupant of the bed can be changed and/or controlled by operation of the system. Such a system can be operated according to a protocol so that the position of the occupant is varied, e.g. rolled from lying on one side to lying on their other side at set intervals, so as to avoid pressure sores or other types of soft tissue damage. The position of the occupant could also be controlled so as to alleviate other medical problems, aid the occupant's respiration and/or aid the drainage of fluid from the occupant's mouth or nose. The protocol used for adjusting the occupant's position may be adjusted in light of measurement data obtained from the support system in a way that is similar to the embodiments in which the system is used with a wheelchair.

The skilled person will appreciate that various aspects and embodiments of the invention can be used in combination and/or conjunction with each other. That is, an embodiment disclosed in relation to a particular aspect of the invention is hereby disclosed in combination with the other aspects of the invention. For example, the aspects and embodiments of the invention relating to a kit or method can make use of the posture support assembly/system of other aspects and embodiments of the invention. Similarly, the posture support assembly/system of aspects and embodiments of the invention can be operated according to methods set out in other aspects and embodiments of the invention. Aspects and embodiments of the invention relating to a support system, kit or method for a wheelchair can be applied to a bed or other person supporting appliance.

BRIEF DESCRIPTION OF DRAWINGS

There now follows, by way of example only, a detailed description of embodiments of the present invention with reference to the accompanying drawings in which:

FIG. 23 illustrates a Jay wheelchair back fitted with a bladder and cover;

FIG. 24 illustrates a wheelchair seat fitted with a bladder and cover;

FIG. 26 illustrates a chair with an expandable support system;

FIG. 27 illustrates a modular expandable body/bladder system;

FIG. 28 illustrates a first example of a module;

FIG. 29 illustrates a second example of a module;

FIG. 30 illustrates a support system in an open/deployed configuration;

FIG. 31 illustrates the support system in a closed/stowed configuration;

FIG. 32 illustrates a support system that has interior deformable portions;

DETAILED DESCRIPTION

Figure 1:
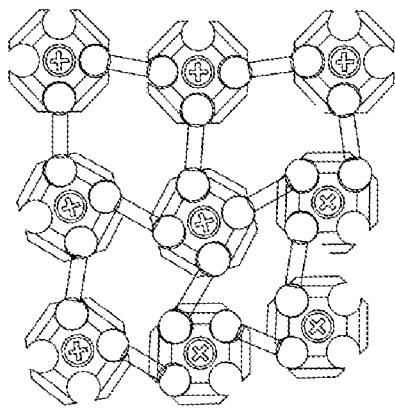
FIG. 1 is an illustration of a section of a known Matrix wheelchair system.
Figure 2:
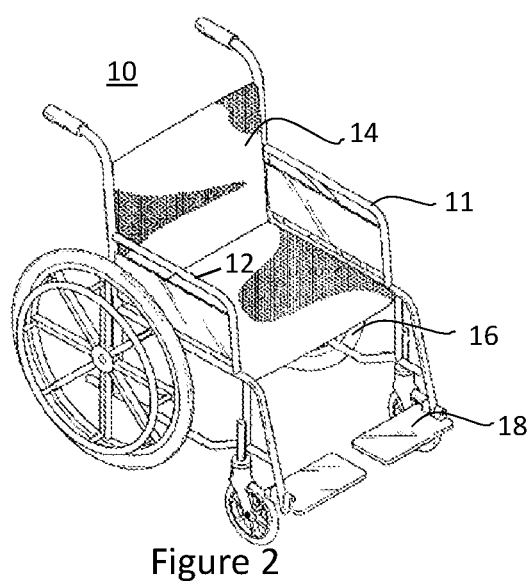
FIG. 2 is an illustration of a generic wheelchair.
Figure 3:
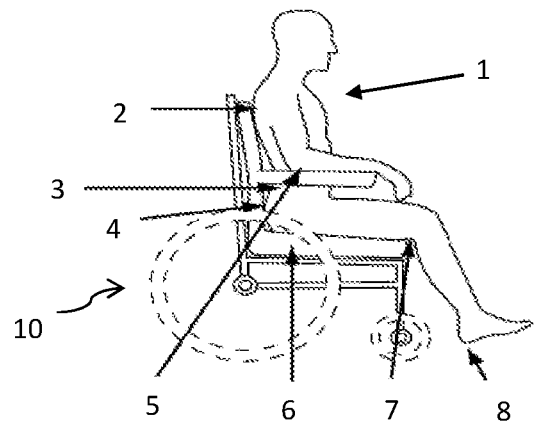
FIG. 3 is an illustration of some contact points on a wheelchair user sat in a wheelchair.

FIG. 2 illustrates a generic prior art wheelchair 10 that supports a user via, for example, a back portion 14, a seat portion 16, foot rests 18 and arm rests 11, 12. FIG. 3 illustrates a wheelchair user 1 seated in such a wheelchair 10. The wheelchair user 1 will generally have several points of contact with the wheelchair 10. For example, the shoulder blades 2, hips 3, tailbone 4, elbows 5, and buttocks 6, back of knees 7, and heels 8. For clarity, the footrests of the wheelchair 10 are omitted from FIG. 3.

Figure 4:
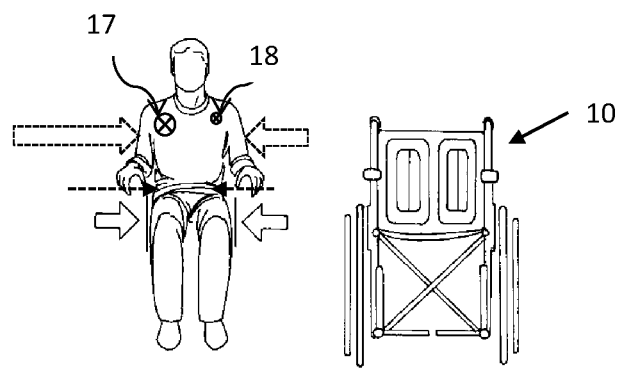
FIG. 4 illustrates example adjustment points for controlling the posture of a user sat in a wheelchair.

FIG. 4 illustrates some example adjustment positions that may be used to correct and/or control the posture of a wheelchair user 1. The arrows in the figure represent a force, pressure or displacement that may be applied the wheelchair user 1 with the size of the arrow being proportional to the magnitude of the force, pressure or displacement. In the example illustrated the arrows are of different sizes to indicate that an asymmetric adjustment can be applied. The crossed circles 17 and 19 illustrate pressures, forces or displacements that can be applied to the back of the wheelchair user 1.

FIG. 3 is an idealised view of a user 1 sitting in a wheelchair 10. For example the wheelchair user 1 is shown sitting in an upright position so that the small of the back of the user 1 is not contacting the back 14 of the wheelchair 10. However, many wheelchair users will be slumped in the wheelchair 10 due to a lack of muscle tone or muscular-skeletal control. The wheelchair user 1 may also have a form of scoliosis that means that various parts of the user's back will be in contact with the back portion 14 of the wheelchair 10 depending on the individual user and the progress of his or her condition.

The wheelchair 10 may be fitted with one or more specific support components or attachments including, for example, a head support, a thoracic support, a neck support, a lumbar support, a foot support, and/or a pommel designed to fit between the legs of a user.

As another example, certain limbs of the wheelchair user 1 may not contact the supports provided on the wheelchair 10 due to, for example, spasticity. In another example, a user 1 may not be able to support their own head such that their head slumps forward or to one side. In this case, their head may not be adequately supported by a head support provided on the wheelchair 10 or the user's head may not be supported at all.

Some aspects and embodiments of the invention are directed at improving the support provided to the wheelchair user 1 when seated in the wheelchair 10 and/or provide for improved posture and/or postural assessment correction and/or adjustment. An adjustment system may be provided, as described hereinbelow that can be fitted to a range of wheelchairs such as the wheelchair 10 illustrated in FIGS. 2, 3 and 4.

Figure 5:
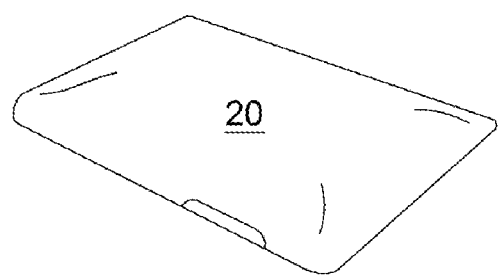
FIG. 5 is a schematic oblique view of an expandable body.

FIG. 5 illustrates an expandable body 20 that is configured to be used with a wheelchair so as to provide support for the wheelchair user 1 that can be adapted and reconfigured according to the individual user's needs and how the user's condition or size may change.

Figure 6:
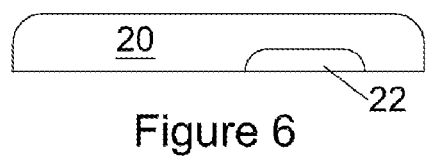
FIG. 6 is a schematic side view of an expandable body.

FIG. 6 is a side view of the expandable body 20. The expandable body 20 has an input means 22 such that the expandable body may expand or contract in response to an input at the input means 22.

In one specific embodiment, the expandable body 20 takes the form of an airbag or bladder and the input means 22 is an air inlet. The skilled person will appreciate fluids other than air can be used to control the degree of expansion of a bladder 20. For example, other gases may be used such as nitrogen gas or the fluid may be a liquid such as water, oil or a hydraulic fluid. Using nitrogen has the advantage that the pressure inside the bladder 20 will remain correct for longer because the rate at which nitrogen passes out the walls of the bladder is slower than for oxygen.

The use of a liquid such as water, oil or hydraulic fluid provides a way for transferring heat into or away from the bladder 20 without requiring an electrical or other heating means in, or near to, the bladder 10. In this way heat can be applied to areas of a user's body as part of a therapeutic treatment, for comfort and/or pain relief, and/or to control the core temperature of the user 1.

Figure 7:
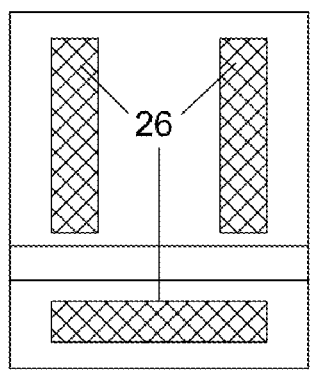
FIG. 7 illustrates the back side of a bladder.
Figure 8:
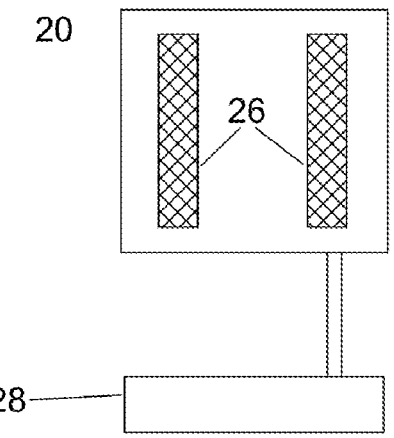
FIG. 8 illustrates a system comprising an expandable body and means to control the degree of expansion of the body.

FIGS. 7 and 8 illustrate the back surface of an expandable body 20 which may be in the form of an airbag/bladder 20. The back surface 24 has one or more strips of Velcro® 26. Although Velcro® is a registered trade mark it is commonly used as a generic term to describe hook and loop engageable material. When the term "Velcro®" is used in the specification the skilled person will understand that generic hook and loop fastening material can also be used.

FIG. 7 illustrates a back view of an expandable body 20 having different sections of Velcro® 26. The sections of Velcro® 26 are arranged so that they can be attached to Velcro® 26 strips on an attachment surface that is attached to or part of a component of the wheelchair 1.

FIG. 8 illustrates an input means 28 in communication with an expandable body 20. If the expandable body 20 is a bladder then the input means 28 is in fluid communication with the bladder. FIG. 8 is a plan view from the back of the system, i.e. the side of the system that will face a wheelchair component.

Figure 9:
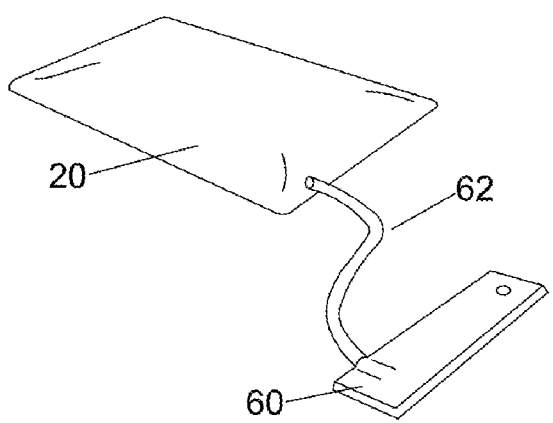
FIG. 9 is an oblique view of a bladder system comprising a bladder connected to a pump.

FIG. 9 is an oblique schematic diagram of a bladder system comprising a bladder 20 connected to a pump 60 via a conduit 62. The pump 60 may be a pump that draws in and compresses ambient air. When the bladders are for use with air they may be termed air bags.

The bladder 20 has an inlet that is connected to the pump 60. The pump 60 may be carried by the wheelchair 1 or it may only be connected to the bladder 20 periodically when the pressure in the bladder 20 is to be adjusted. Instead of, or as well as, a pump 60, compressed gas could be used such as a pressurised cylinder of gas.

The bladder 20 may be provided with a separate outlet (not illustrated) for the release of gas or the inlet may also be configurable to act as an outlet. For example the bladder 20 may be provided with one or more valves so that the pressure inside the bladder 20 may be adjusted.

Figure 10:
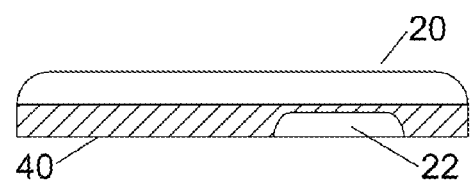
FIG. 10 is a schematic side view of an expandable body with a foam layer.

FIG. 10 illustrates an embodiment of the bladder 20 that contains or is connected to a backing such as a shape memory foam 40. The shape memory foam 40 may be configured so that it is on a side of the bladder 20 that is to be in contact with the wheelchair user 1. The shape memory component may comprise viscoelastic polyurethane foam. The use of such shape memory foam 40 allows better contact with the contours of the portion of the wheelchair user's body that is to be supported.

Figure 11:
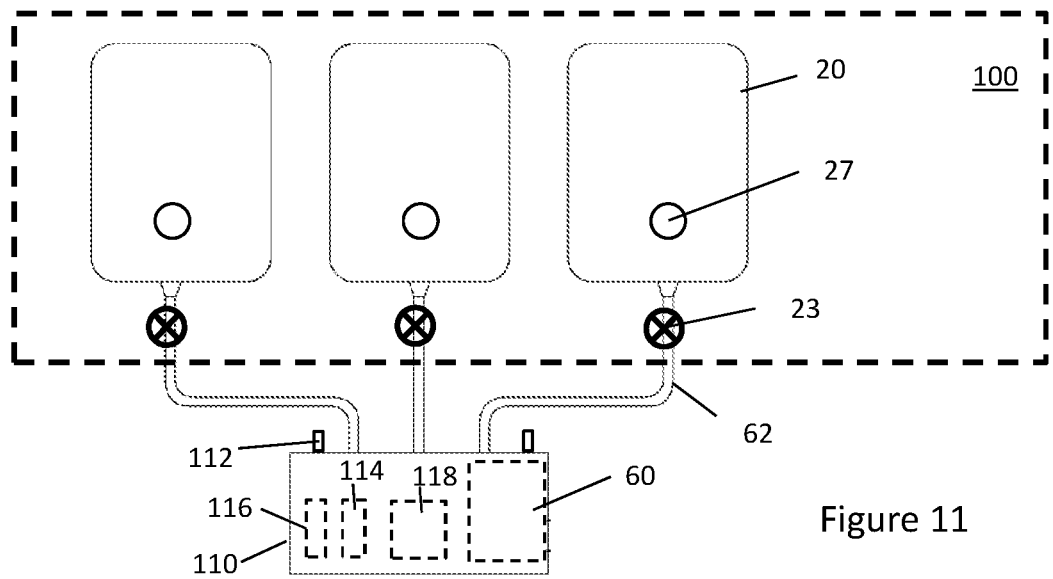
FIG. 11 is a schematic of a bladder system.

FIG. 11 illustrates a system 100 in which multiple bladders 20 are connected to the same pump 60. The number of bladders 20 can be changed and/or reconfigured according to the needs of the wheelchair user 1. Additionally, damaged bladders 20 or conduits 62 may be replaced without needing to replace the whole system.

The pump 60 may be contained in a base unit 110, for example, a housing. Such housing may be attached to the wheelchair or other person supporting appliance. In one example, the housing is a rigid housing. The base unit 110 may have a plurality of ports/connectors 112 to which bladders 20 may be connected by conduits 62. The base unit 110 can have additional ports 112 so that the bladder system 100 may be expanded, i.e. the number of bladders increased, according to the needs of the user. The base unit may also house a processor 116, a power supply 118, and a wireless communication component 114, for example a Bluetooth module.

The pressure in each bladder 20 may be selectively controlled via a valve 23 that is present in the conduit 62 associated with that bladder 20, the bladders 20 itself, or in the base unit 110, e.g. in a part of the pump 60 that is in fluid connection with the conduit 62 connected to that bladder 20. In one embodiment the valve 23 is in the conduit 62 so as to make it easier to replace or service the valve 23. Similarly, a pressure sensor 27 can be situated in one of several places that is in fluid or mechanical communication with a bladder 20, for example, the sensor 27 may be within the bladder 20, connected to the outside of the bladder 20, within the conduit 62, connected to the outside of the conduit 62 and/or within the pump unit 60 in the portion that is in fluid connection with the conduit 62.

Advantageously, the sensor 27 is a textile flexible pressure sensor. Such a sensor senses pressure from the entire surface of the sensor and is bendable. Measurement of the face pressure distribution on the sensor 27 is achieved by sensing capacitance changes caused by pressure. Since the sensor 27 is made from a flexible textile it can be used to cover a large area of the expandable body/bladder 20. For example, the textile sensor could be used to cover, substantially, equal or greater than 20%, 30%, 40%, 50%, 60%, 70%, 80%, 90% or substantially the entire surface of the expandable body/ bladder 20. In one example, the bladder 20 may be made of the flexible pressure sensor or a portion of the bladder 20 is made of the flexible sensor, for example, substantially, equal or greater than 20%, 30%, 40%, 50%, 60%, 70%, 80%, 90%.

Former commercialized pressure sensors are coin shaped and made of PCB substrates or PET films, making them difficult to bend or deform. Since such commercial sensors are stiff, there is the potential to cause irritation to user if they are used on the bladder system. This problem is alleviated by the use of flexible textile sensors.

Textile flexible pressure sensors can be made using highly elastic polymeric material with electrical wires embed in the material. For example, sensors developed by LG Innotek use highly elastic polyurethane material. When an external force is applied to the sensor, electric poles inside the wires detect deformation to of the expandable body to determine pressure.

FIG. 27 illustrates a modular system that comprises one or more modules 300 that are arranged to be in wireless communication with a controller 320. Each module 300 comprises an expandable body 20 and a means to alter the degree of expansion of that body. The controller 320 is arranged to control the individual modules 300. The controller 320 may be a suitably programmed electronic device such as for example, a personal computer, laptop, PDA, remote control, or mobile telephone. In one particular example, the controller 320 comprises a mobile phone having an application ("App") for controlling the modules. The controller 320 may be equivalent to, or have the same functionality, as the controller 200 described in relation to FIGS. 16-22.

For simplicity, the modules 300 are illustrated deployed on a mattress 330 but they may be deployed on any person supporting appliance.

Each expandable body may be an inflatable bladder 20 and the means to alter the degree of expansion may be a source of compressed gas such as a pump 60. In this case the bladders 20 do not need to be connected to a common pump 60 since each bladder 20 is in fluid communication with its own individual pump 60.

Each module may also have one or more of the following: a sensor 27 to measure the pressure exerted by the expandable body/bladder 20, a power source 118, a wireless communication component 114 and a processor 116. Typically, the power source 118 comprises one or more batteries which are used to supply electrical energy to the pump 60 (when one is used). The power source 118 may also be used to supply electrical energy to the processor 116, communication component 114 and/or the valves 23.

The main function of the controller 320 is for setting up the system, for example, by setting and monitoring the degree of expansion of the expandable bodies/bladders 20. Generally, the controller 320 is used by, for example, physiotherapists and occupational therapists as they can diagnose and set the right setting for the patients. The main function of the processor 116 is to collect data relating to postural movement of the user and synthesize data for the system to understand the user better. The system can then react smartly to either: potential deflation over time, which alerts the system to self-inflate to the correct setup, or evoke oscillation when the user stays static for too long. However, the division of what functions are performed on what component, the processor 116 or the controller 320, is a design choice that can be varied. For example, in some cases, raw sensor data could be communicated to the controller 320 for processing.

FIG. 28 illustrates a first example of a module 300. Such a module 300 can be deployed alongside other modules such as is illustrated in FIG. 27. In the first example of the module 300, the pump 60 is contained within a housing 119 and is in fluid communication with an associated bladder 20 via a conduit 62. The housing 116 may also contain other components such as one or more of: the wireless communication component 114, the processor 116 and the power source 118.

The components need not be contained by a housing and could be supported on a support means (not illustrated). The components may be partially supported and partially housed. In one example, part of one or more of the components may be within a housing with the remaining part of the one or more components being external to the housing. In another example, one or more of the components may be fully contained within the housing with the remainder of the components being external to (or partial external to) the housing whilst being supported by the housing. FIG. 29 illustrates a second example of a module 300. Such a module can also be deployed alongside other modules such as is illustrated in FIG. 27. In the second example of the module 300, the pump 60 is at least partially contained within a backing 40 that is attached to the bladder. For example, the pump 60 is housed within, or supported by, a backing 40 such as foam (e.g. a shape memory foam). The backing 40 may also contain/support other components such as one or more of: the wireless communication component 114, the processor 116 and the power source 118.

Since the modules 300 (such as the first and second example of the modules) do not have any physical connection to each other, or another unit, there is a greater freedom as to how they may be configured on a person supporting appliance.

The wireless communication component 114 of each module 300 is configured to communicate with a controller 320. The controller 320 controls the degree of expansion of the expandable body/bladder 20 of the module 300. In particular, the expandable body/bladder 20 is controlled in response to a signal generated from the pressure sensor 27 associated with the expandable body/bladder 20. The sensor signals may be sent to the controller 114 via the wireless communication component 114.

The modules 300 may also communicate with each other. In this way the modules can be considered to form an "Internet of things". The modules 300 may be able to detect the positions of each other such that the positions of the modules 300 (e.g. as on the mattress illustrated in FIG. 27) can be related to the controller 320. If the controller 320 has a display, the display can be updated if one or more of the modules 300 are moved. In another set-up, the modules 300 are configured to communicate with each other to move the user of a support appliance (e.g. change the users posture.

In FIG. 27, as an example only, the display of the controller 320 indicates that the degree of expansion of a particular individual module 300a is being controlled and/or monitored.

The expandable bodies/bladders 20 may be fitted, attached or otherwise connected to a rigid structure. In one embodiment, the rigid structure may be an existing component of a wheelchair or a portion thereof. The component may be, for example, a head support, a thoracic support, a neck support, a lumbar support, a foot support, and/or a pommel designed to fit between the legs of a user. In another embodiment the rigid structure is fitted on top of an existing component. In this case, in use, the rigid structure will be between the existing component and the wheelchair user 1.

Figure 12:
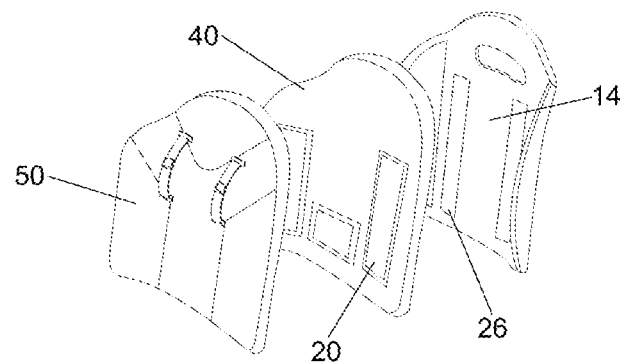
FIG. 12 is an exploded schematic illustration of a bladder system fitted to a wheelchair back.

FIG. 12 shows an exploded view of a support system fitted to a back component 30 of a wheelchair 1. The support system comprises one or more pieces of memory foam 40 that can be fitted to the wheelchair back 14 with the bladders 20 to be positioned under the memory foam 40 according to the needs of the wheelchair user 1. In other embodiments, the memory foam 40 is replaced by some other material, for example foam that is not memory foam or the material may be dispensed with altogether. In one embodiment bladders 20 are attached directly to the wheelchair back 30, for example using a Velcro® or Velcro-type (hook and loop) attachment system. Generally, a cover 50 is then placed over the system and/or wheelchair back 14.

Figure 13:
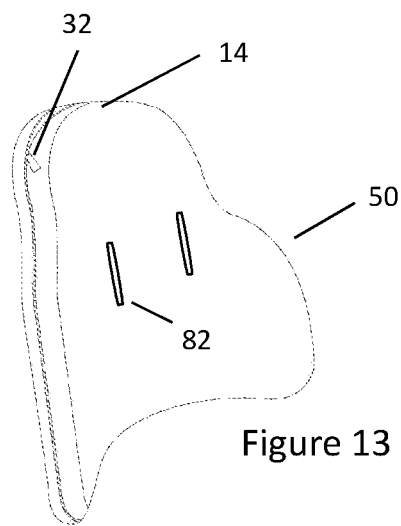
FIG. 13 is an oblique view of a cover, having a zip fitted, to a wheelchair back.
Figure 14:
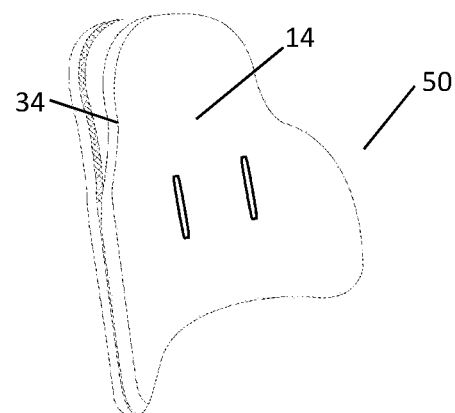
FIG. 14 is an oblique view of a cover, having a releasable material, such as Velcro® fitted to a wheelchair back.

FIG. 13 illustrates a wheelchair back 14 in which the cover 50 is attached to the wheelchair back 30 via a zip 32 that runs, for example around the edge or periphery of the wheelchair back 30 or a substantial portion thereof. FIG. 14 illustrates a similar system in which the attachment is by means of a Velcro® like attachment. The periphery of the cover 50, or a portion thereof, may alternatively or additionally be elasticated so as to hold the cover 50 in place. Such systems allow the cover 50 to be easily removed for washing or replaced with a different cover.

In one embodiment, the cover 50 has one or more slits or openings 82 which allow access to the underlying bladders 20 when the cover 50 is covering the bladders 20. The slits 82 allow a person, such as a carer or healthcare professional, to access the bladders 20 so that they can be repositioned without removing the cover 50. For example, the slit 82 may be of a sufficient size so that some or all of a person's fingers may be able to reach through the slit 82 to manually reposition the bladders 20.

Similar arrangements can be used for other components of the wheelchair 10 so as to provide variable and controllable support to different regions of a wheelchair user 1. For example the bladders 20 can be used to provide variable lumbar-sacral support to the sides of the user 1 in the hip region. In another example the bladder system may be used to provide support that corresponds to the degree of knee flexure presented by the wheelchair user 1. The positioning of a wheelchair user's limbs can be problematic if the user 1 suffers from spasticity (as is often present in suffers of cerebral palsy and various types of multiple sclerosis). In such cases, the current system is advantageous since it can be adapted to meet an individual's specific body form and degree of spasticity presented.

Figure 15:
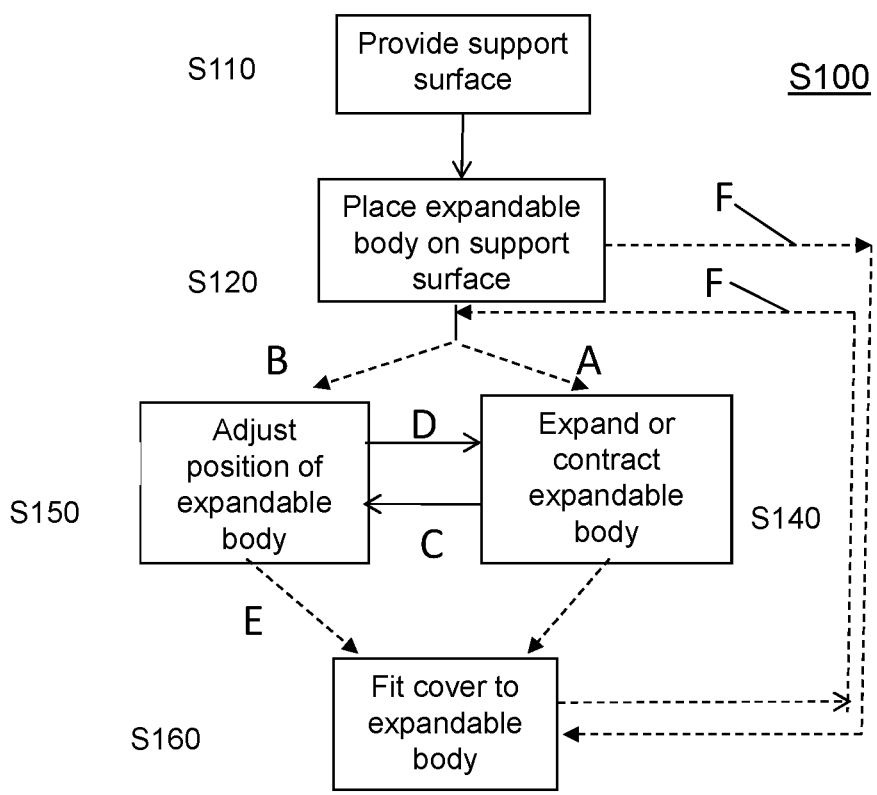
FIG. 15 is a flow diagram of a method of fitting an expandable body to a wheelchair component.

FIG. 15 is a flow diagram of a method S100 of providing adjustment of a support for a wheelchair user 1.

In step S110 a support surface is provided. The support surface may be the surface of a wheelchair component such as, for example, a wheelchair back 14 or side portion. The support surface could also be provided by an intermediate component that is attached or attachable to the wheelchair component. For example, the support surface may be provided by a rigid structure or a piece of material on top of a rigid structure. The support surface is generally provided with some releasable means of attachments such as a Velcro®.

In step S120 one or more expandable bodies 20 are placed on the support surface. The, or each, expandable body 20 may be an airbag or bladder or some other form of expandable body 20. In one embodiment, an expandable body 20 is placed on the support surface at a place chosen so that the expandable body 20 is able to provide support to a specific part of a wheelchair user 1 when using the wheelchair 10. The placement may be performed by a medical professional, wheelchair technician or a carer. The position of the expandable body 20 on the support surface may only be approximate or an estimate of where the medical professional/technician believes that the expandable body 20 will best provide support for the individual wheelchair user 1. This may be based on personal experience of the health professional/technician or such a person may use historical data to identify positions that may be suitable. Such historical data may include measurement data from a previous use of the support system with the specific wheelchair or a specific user 1. Historical data, e.g. protocol data and/or measurement data, may be available from different support systems, different wheelchairs, different users and/or different users with the same or different medical condition. It will be appreciated that the type of historical data can be any combination of these categories, for example, the historical data may relate to the specific type of wheelchair used and/or wheelchair users having the same or similar medical condition in the same age range or weight range as the specific wheelchair user 1 in question. The historical data may indicate that, say, an adolescent suffering from cerebral palsy may require a certain pressure range or pressure applied to specific parts of the wheelchair user's body. The historical data may indicate that certain parts of the wheelchair user's body should be moved by a specific amount or range. This required movement could be expressed in dimensions such as angle, and/or distance and/or co-ordinate data. The dimensions, position and/or orientation of the expandable body 20 could be changed in accordance with such data. For example, the data may indicate that a particular support body should be adjusted to provide a specified degree of support (e.g. a certain number of millimeters).

After the expandable bodies 20 have been placed on the support surface, the wheelchair user 1 may be seated in the wheelchair 10 so that a check can be made on the appropriateness of the support provided by the expandable body 20.

Following route A illustrated in FIG. 15, at step S140 the degree of expansion of the expandable body 20 is controlled. That is, the expandable body 20 may be expanded or contracted. In the case of an airbag or bladder which holds fluid the expandable body 20 may be inflated or deflated. Following expansion or contraction it is possible, in step S150, to adjust the positon of the expandable body 20 (following route C illustrated) to a position that may be more appropriate for the degree of expansion of the expandable body 20. The process of expanding or contracting the expandable body S140 and adjusting the position of the expandable body S150 may be an iterative process that improves the suitability of the support provided by the expandable body 20.

The first step following the initial placement of the expandable body S120 may be to adjust the position of the expandable body S150 via route B and then expand or contract the body S140 via route D.

In one embodiment, once the expandable body 20 has been suitably adjusted, a cover 50 may be fitted over the expandable body 20 in step S160. However, in this case it may be necessary for the wheelchair user 1 to vacate the wheelchair 10 if the expandable body 20 is provided on a support surface associated with the wheelchair back or seat 16. If the support surface is associated with some other component, such as arm rests 11, 12, headrests or feet rests 18 then it may be possible to fit the cover 50 without the wheelchair user 1 having to vacate the wheelchair 10. Alternatively, if (following route F illustrated) the cover 50 is fitted to the expandable body 20 before the degree of expansion or the position of the expandable body is modified, then it will not be necessary to move the wheelchair user 1 out of the wheelchair 10. Following this alternative route can be highly advantageous since it avoids unnecessary manual handling of the wheelchair user 1. Also it is easier to fit a cover 50 over an expandable body 20 on a support surface when the expandable body 20 is unexpanded or expanded to a degree less than the degree of expansion when the body 20 is in a deployed or otherwise more expanded state. This allows the cover 50 to have a tight/secure fit when the bodies are in the expanded/deployed state but allows easy fitment when the expandable bodies 20 are in their unexpanded/stowed state.

Figure 16:
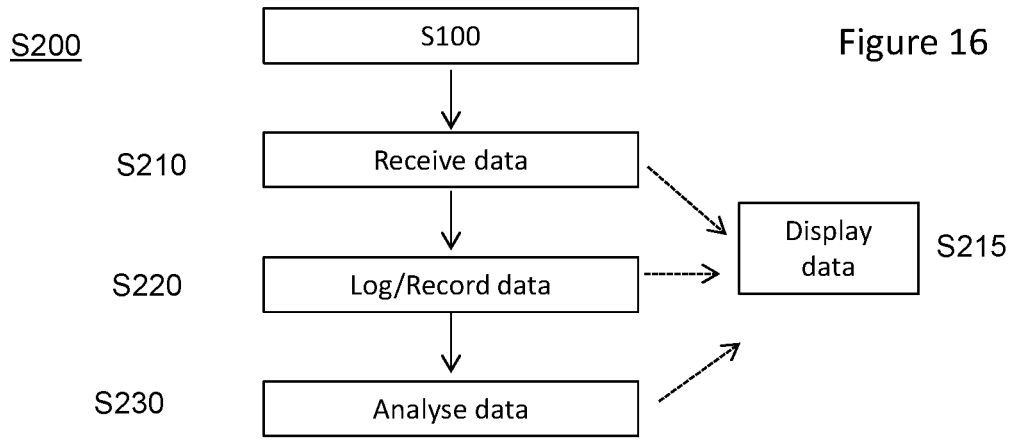
FIG. 16 is a flow diagram of a method of receiving measurement data.

FIG. 16 is a flow diagram of an example method S200 for processing measurement data received from the expandable body 20.

At step S210 measurement data is received from the expandable body 20. For example, the data may be generated once the expandable body 20 has been fitted to a wheelchair component according to method S100 and a wheelchair user 1 is seated in the wheelchair 10. The measurement data may be received by a computing device such as a computing device associated with a user interface 200. The user of the user interface 200 may be the wheelchair user 1, a carer of the wheelchair user 1 and/or a medical practitioner such as a physiotherapist, occupational therapist or suitably qualified doctor or nurse, or a wheelchair technician.

The user interface 200 may be in wireless communication with a signal output of a bladder system so as to receive measurement data from sensors associated with the expandable body. The user interface 200 may also be in wired connection with the data output e.g. by electrical wires or optical fibres. The user interface 200 can be a bespoke user interface or it may be a suitably programmed mobile device such as a mobile telephone, PDA, tablet, laptop or similar. The software may be available as an "App" which may be pre-installed on the device or downloaded/purchased and/or updated via the Internet. FIGS. 19-22 illustrate a user interface 200 in the form of a suitably programmed mobile phone.

At step S215 the received data may be displayed on the user interface 200. In step S215 the displayed data may take the form of real-time or substantially real-time values, for example, the displayed data may take the form of a digital gauge.

At step S220 the received data is recorded. The recording step 220 may occur in place of display step S215 or as well as display step S215.

At step S230 the received data may be analysed. For example the received data may be used to produce derived information that can be displayed and/or stored.

The skilled person will appreciate that not all of the steps illustrated in FIG. 16 need to be present in method S200. For example the user interface 200 may be configured so as to display real time data but not to record the data, for example, such data may be communicated to a further device for storage and/or further processing. In another example the data may be recorded without being displayed. For example the data can be subsequently downloaded and/or communicated for processing and/or display at a later time.

Figure 17:
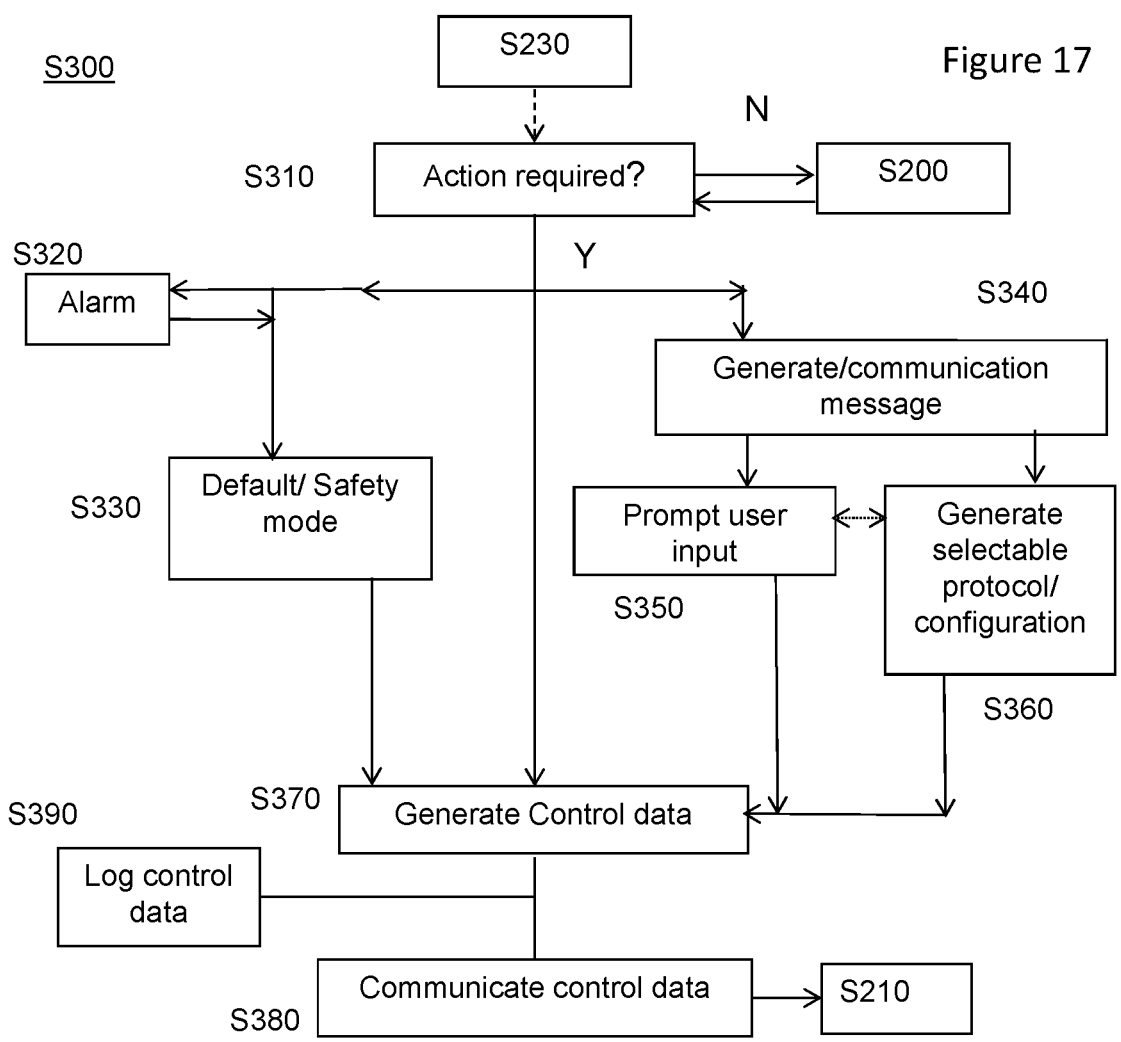
FIG. 17 is a flow diagram of a method of generating control data.

FIG. 17 is a flow diagram of a method for generating control data S300.

In step S310 it is determined that action is required in relation to one or more expandable bodies 20 or the posture of a wheelchair user 1 sat in a wheelchair 10. For example, the determination may be made from an analysis of received and/or logged measurement data according to method S200.

In another example, the determination that action is required may be due to an assessment by a medical professional with or without the data provided by the analysis of step S230. Whilst, and subsequent to, the determination of whether action is required, data may continue to be received, logged, analysed and/or displayed according to method S200.

In step S320 an alarm signal may be generated when an analysis of received data indicates that action is required. Such an alarm may be an audible and/or visible alarm.

In step S340 a message may be generated as well as, or instead of, an alarm. The generated message may be stored for future access, for example, the message may be accessible when a user of the user interface 200 is reviewing the suitability of the support provided by the support system. The message may also be directly communicated to a user for immediate attention. Whether an alarm is generated, a message is generated, or whether any such message is stored or immediately sent for the attention of a user, may depend on the extent of the action that is required and its impact on the wellbeing of the wheelchair user 1. For example, if an action is required to mitigate serious effects on a wheelchair user's 1 respiratory system then an alarm may be generated and/or a prioritised message sent.

In step S330 it may be determined that the bladder system 100 should be placed in a default or safety-mode configuration that corresponds to a posture of the wheelchair user 1 that is likely to put the wheelchair user 1 in a relative position of safety until the wheelchair user 1 can be attended to. In such a situation, the determination that a default/safety configuration is a suitable response to step S310 results in the generation of control data in step S370 that can be communicated to the bladder system 100 in step S380.

Following the generation of a message in step S340, in step S350 the user interface 200 may prompt a user to provide data input that will alter the configuration of the bladder system 100, for example, to expand or contract one or more of the expandable bodies 20. At step 360 the user interface 200 may prompt a user to select one or more of a predetermined configuration or protocol.

At step S370, control data can be generated in response to a user input or and/or a user selection of a predetermined configuration or protocol. In one variation of the method, a user may select a particular predetermined configuration or protocol and then adjust such a configuration or protocol by further user inputs.

At step S380 the control data is communicated to the support system so that the one or more expandable bodies 20 may be expanded or contracted accordingly. The control data may comprise data relating to the position of one or more bladders 20 on the surface of a wheelchair component. In this case the control data is not communicated to the bladder system 100 but may be displayed on the user interface 200 as, for example, instructions to a user. Control data regarding the degree of expansion of one or more expandable bodies 20 may also be displayed on the user interface 200 as, for example, instructions to a user, instead of being communicated to the expansion system.

In step S390 the generated control data is stored. This step may occur irrespective of whenever the control data is communicated to the bladder system 100. The stored control data may then be made available as historical data for use by a user when determining the future reconfiguration of the bladder system 100 or for the reconfiguration of different bladder systems.

Figure 18:
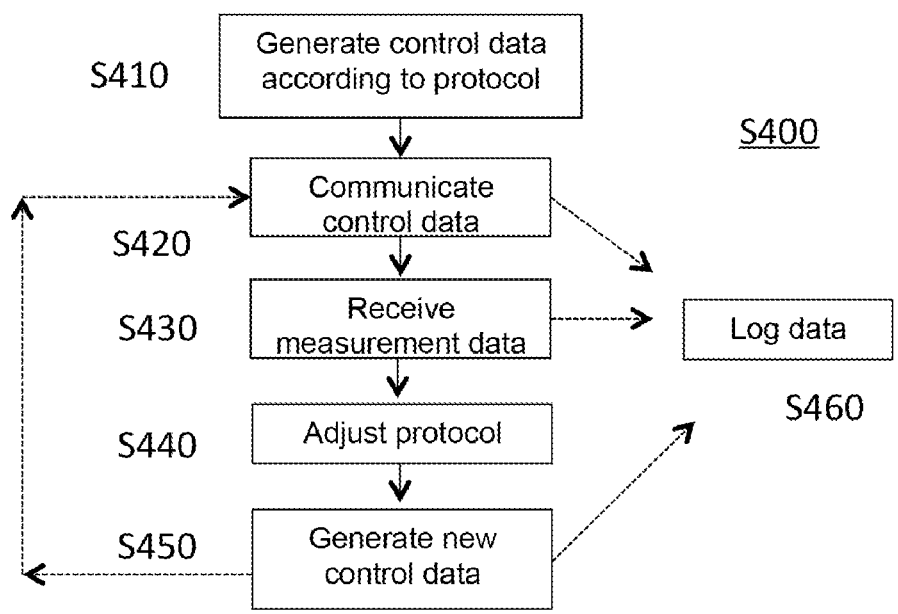
FIG. 18 is a flow diagram of a method of adjusting protocol data.

FIG. 18 is a flow diagram that illustrates a method S400 of monitoring a protocol for a wheelchair user 1. For, example, method S400 may be used to monitor the efficacy of a protocol. The protocol may comprise data values relating to pressures to be set in one or more bladders 20 that are arranged to support different regions of a wheelchair user's body. The protocol may also include dynamic information relating to the cycling of the pressure in an individual bladder or cycling the pressures between a plurality of bladders 20. The protocol data may also give relative or absolute pressure differences between various bladders of a multi bladder system 100.

At step 410, control data is generated according to a protocol. At step S420 the control data is communicated to the support system and the degree of expansion of the expandable bodies 20 is controlled according to the control data. At step S430 measurement data is received from sensors associated with the one or more expandable bodies 20. At step S440 a user may adjust the protocol at the user interface 200. At step S450 new control data is generated according to the adjusted protocol and the new control data is then communicated to the data system by returning to step S420.

At each stage of communicating control data, receiving measurement data, adjusting the protocol, and generating new control data the associated data may be stored in step S460.

Figures 19, 20:
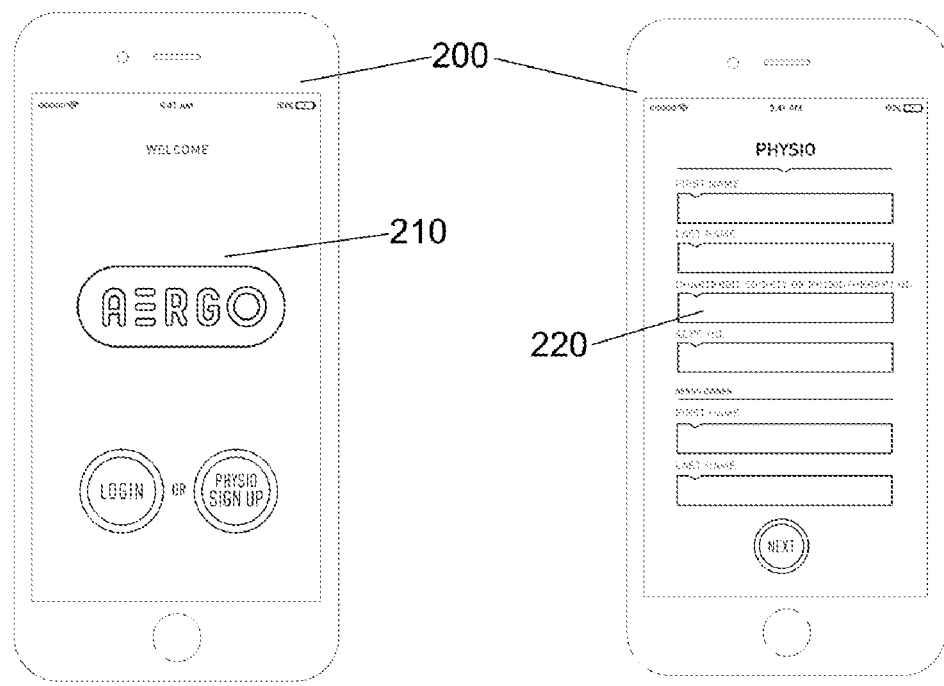
FIG. 19 illustrates a login graphical user interface.
FIG. 20 illustrates a registration graphical user interface.

FIG. 19 illustrates a user interface 200 having an example login graphical user interface (GUI) 210. The login GUI 210 allows a user registered with the user interface 200 to log in. The login GUI may also allow a user, such as a physiotherapist, to register or "sign up" with the interface 200.

FIG. 20 illustrates the interface 200 with a "physio" GUI 220. The physio GUI 220 allows a physiotherapist to enter information that will identify him or her as a bona fide physiotherapist, for example, the physio GUI may require the physiotherapist to enter membership or reference numbers relating to one or more appropriate regulating or governing professional bodies. Similar GUIs may also be available on the interface 200 for different types of users, for example doctors, nurses, wheelchair technicians, wheelchair users and carers of the wheelchair user 1. According to the category of the user, various permissions may be granted to the user. For example a physiotherapist may have full access to review historical data, protocols and to adjust the support system of a wheelchair 10. A doctor or a nurse may have permissions that allow them to view historical data but not to adjust the wheelchair support system. Other users, such as the wheelchair user 1 and/or his carers may be able to review historical data and have limited control of the adjustment of the support system. For example the control of the support system may be confined within certain ranges. The extent of the range may also be chosen according to the user for example the physiotherapist may have a very large range for adjustment of the support system, whereas non-medically qualified users may have narrower ranges within which they may adjust the support system.

Figure 21:
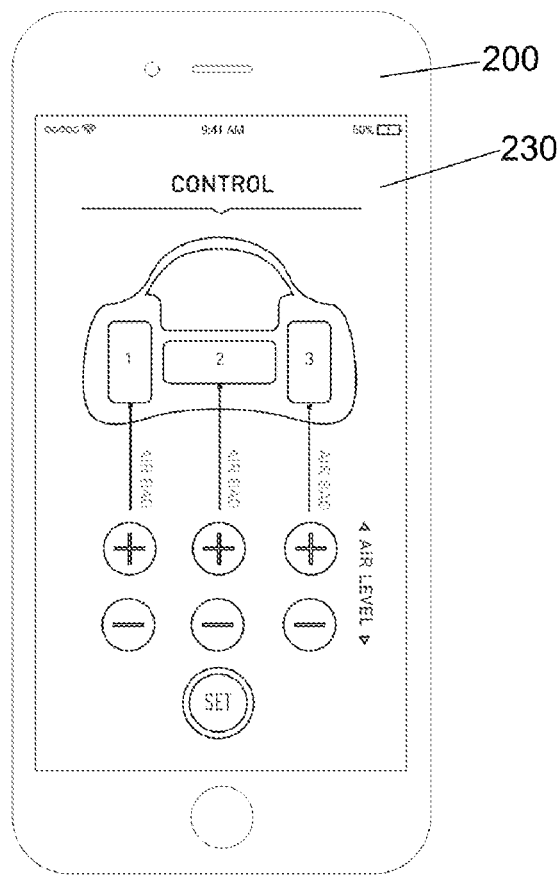
FIG. 21 illustrates a control panel graphical user interface.

FIG. 21 is an illustration of an example control GUI 230. In the example illustrated, control may be provided over any of expandable bodies 20, such as airbags 1, 2, 3 that are in position on a wheelchair component. In the example illustrated, the wheelchair component is a back rest 24 and the user may increase or decrease the pressure of air within any of the airbags 1, 2, 3. Different control GUIs 230 may be available and/or selectable, for example, there may be different control GUIs for other components such as a headrest, footrest 18 or leg panel for example. The control GUI 230 may provide or display all of the wheelchair components to which a bladder system 100 has been fitted. A user may then zoom in or select the wheelchair component(s) that is to be adjusted. In one particular embodiment, the expandable bodies/airbags 1, 2, 3 may have an identifying code that may be transmitted to/interrogated by the user interface 200 such that the type of airbag may be identified. For example there may be different types of airbag according to which type of wheelchair component the airbag is attached to or where on the wheelchair component the airbag is attached. This identifying information may be used so as to determine the range of acceptable pressures that may be used with that particular airbag. As another example, the unique identifying code may be used to display an appropriate schematic for the wheelchair component with which the airbag is associated.

Figure 22:
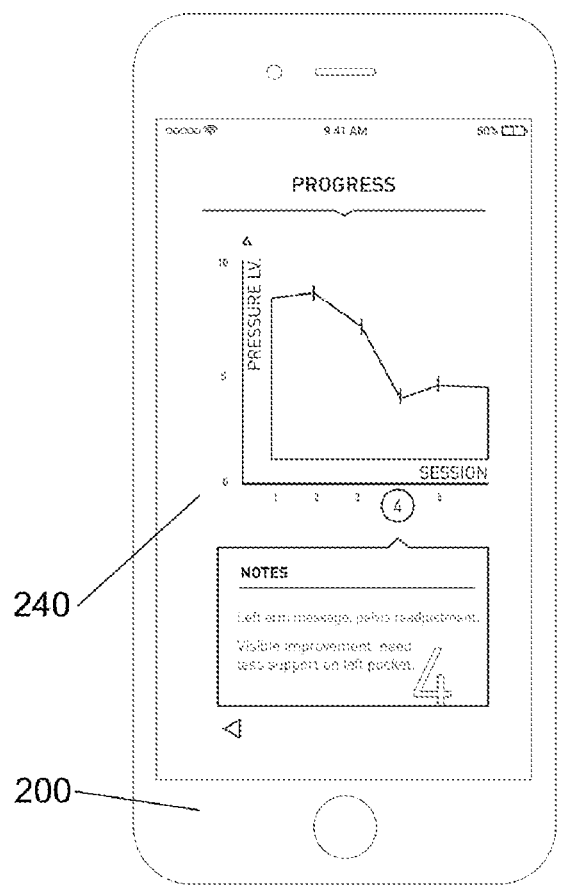
FIG. 22 illustrates an analysis graphical user interface.

FIG. 22 shows a user interface 200 having a "history" or "analysis" GUI 240. For example, historical data may be displayed on the GUI 240 in various forms. A form illustrated is that of a graph, however, other forms such as a list, table or a text description may be displayed. The history GUI 240 may also have a region in which a user may make or view notes on a wheelchair user 1, for example the notes could include information on the response of a wheelchair user to a particular protocol.

FIG. 23 illustrates a system in which airbags have been fitted to a proprietary Jay back 30 system and fitted with a cover 50. FIG. 24 illustrates an airbag system fitted to a seat component 16 with a cover 50 fitted.

Although aspects and embodiments of the invention relate to a posture support system for use with a wheelchair, the posture support system may also be used together with other appliances. In this case the posture support system may be more generally termed a "positioning system" or simply a "support system". For example, the system may be used with a bed (e.g. a hospital bed), a static chair or with more specialist support equipment such as a side-lying board or standing frame. The posture support system of the current invention is highly adaptable so that it can be fitted to such equipment with little or no modification. This advantage is the result of the system being highly adjustable simply by moving one or more expandable bodies 20 to the required position(s) and adjusting the degree of expansion of the one or more bodies 20 to the required levels.

FIG. 25 illustrates the deployment of a support system on a bed 150; whereas FIG. 24 illustrates the deployment of a support system on a chair 170 (the example illustrated is an armchair but other types of seating support structures may be used). The support systems may be the same support system as previously described in relation to a wheelchair. In FIGS. 25 and 26, multiple expandable bodies 20 are shown deployed in relation to an appliance user 1A; however, a single expandable body 20 may be used by itself. For clarity, FIGS. 25 and 26 illustrate only the expandable bodies of a support system. The support system may also comprise the pump 60, conduits 62, valves 23, one or more covers 50 and/or shape memory foam 40 that have been described in relation to FIGS. 8-14.

Figure 25A:
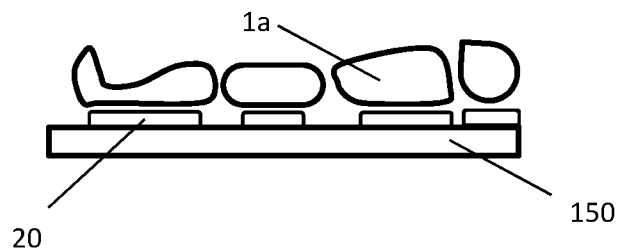
FIGS. 25A-25E each illustrate a bed with an expandable support system.

FIG. 25A illustrates expandable bodies 20 placed underneath a user 1A on a bed 150. For example, the expandable bodies 20 may be placed on top of a mattress. In other embodiments the expandable bodies may be placed underneath a mattress or cushion such as a shape memory foam mattress or cushion. In another embodiment the expandable bodies 20 are placed underneath a shape memory mattress or cushion and on top of a further or "main" mattress. In this case, the shape memory mattress or cushion may be thinner than the mattress that is underneath the expandable bodies 20. A thinner mattress or cushion will generally conform more closely to the shape of the underlying expandable bodies 20. One or more expandable bodies 20 may be placed underneath different regions of the appliance user 1A, for example, as is illustrated in FIG. 25A, underneath the lower legs, the upper legs, the torso and the head of the user.

Figure 25B:
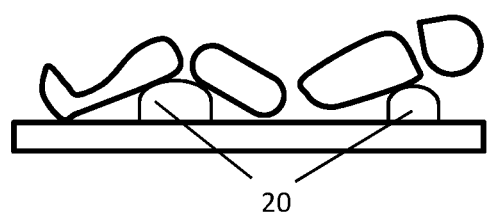

FIG. 25B illustrates two expandable bodies 20 in an expanded/deployed configuration. In the case illustrated, the bodies 20 have been used to support the user's knees and shoulders in a raised position. Of course, the number and position of the expandable bodies 20 can be altered in the same way as has been previously described in relation to a wheelchair 10. In particular, the positioning of the expandable bodies 20 can be adjusted following method S100 illustrated in FIG. 15.

Figure 25C:
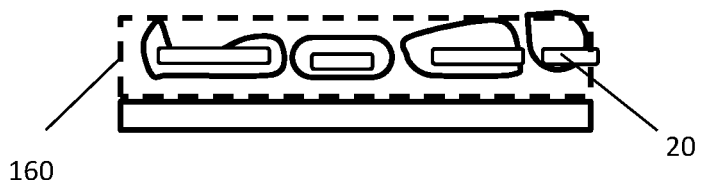

FIG. 25C illustrates expandable bodies 20 that are positioned along a first side of an appliance user 1a. Again, there is freedom to change the number and positioning of the expandable bodies to match the individual requirements of the user 1a. FIG. 25C illustrates a cot side 160, such as may be provided on a hospital bed. The cot side 160 may be used to provide a rigid structure to which the expandable bodies 20 can be attached. Alternatively, an attachment surface may be attached or otherwise connected to the cot side 160. Such an attachment surface may comprise a sheet of, or one or more portions, of Velcro® 26 or other releasably engageable material. It will be appreciated that other types of support can be used to which the bodies 20 can be attached. In one example, one or more right-angled brackets can be placed on a horizontal surface of the bed 150 or attached to a horizontal attachment surface on the bed 150 so as to provide an upright portion to which the expandable bodies 20 can be attached.

Figure 25D:
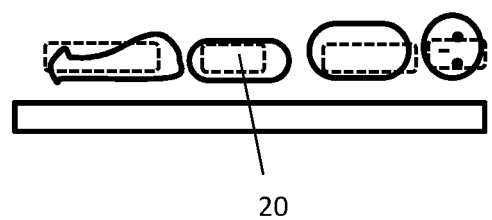

FIG. 25D illustrates expandable bodies 20 on a second side of the user 1a. In this case the expandable bodies 20 have been deployed so that they have expanded and moved the user 1a so that the user 1a is lying on one side. That is, the expandable bodies 20 have been expanded in a direction that is out of the paper of the illustration of FIG. 25D. The expandable bodies 20 can be deployed on both sides of the user 1a and a different configuration of expandable bodies 20 may or may not be used on the different sides of the user 1a. By having one or more expandable bodies 20 on different sides of a user 1a, the user 1a may be turned to face first one side and then a second side, or to face upwards. In such a way the position of the user can be varied so as to avoid soft tissue damage such as bed sores, provide increased comfort to the user, and/or improve drainage of fluid from the user's mouth. The turning of the patient can be controlled, e.g. using the interface 200 (illustrated in FIGS. 19-22) to follow a cycle. The degree of turning, the frequency and the period of time between turns are variables that can be defined and controlled/customised.

Figure 25E:
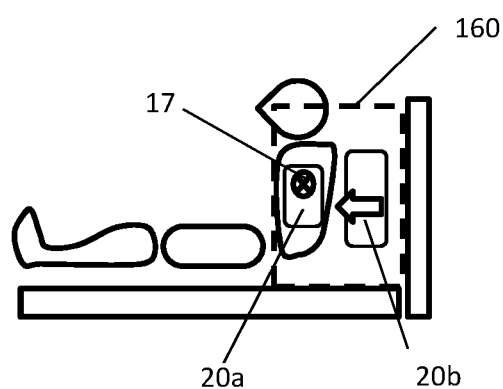

FIG. 25E illustrates a user 1A whose torso is in a raised positon. The torso may be supported, in part, by a raised section of the bed 150 or by a headboard or other structure. An expandable body 20b may be placed behind the torso, neck and/or head of the user so as to adjust the angle of these body parts. In FIG. 25E, the expansion of body 20b will be in the direction going from right to left as indicated by an arrow. A further expandable body 20a may be provided at the side of the user 1a with the expansion of the body 20a being into the plane of the paper as illustrated by crossed circle symbol 17. The expandable body 20a at the side of the user 1a may be supported by a cot side 160 or other structure.

FIG. 26 illustrates a static chair 170 on which a support system has been deployed. The chair 170 may, as illustrated, have a back portion 14A, armrests 11A, 12A and a seat 16A. The chair 170 may also have other components such as a footrest or a raised or raiseable portion that may support the lower legs of a user and to which an expandable body 20 may be attached. The expandable bodies 20 may be deployed and operated in the same way as has been described in relation to a wheelchair. In FIG. 26, the expandable bodies 20 illustrated as having no fill pattern are configured to expand in the direction out of the plane of the paper. The expandable bodies 20 illustrated as having a hatched fill pattern are configured to expand in the direction that is perpendicular to the other bodies illustrated.

For both the bed 150 and the static chair 170, or indeed any other suitable support apparatus, measurement data can be obtained from the support system and be recorded and/or displayed as set out in method S200 (illustrated in FIG. 16). The one or more expandable bodies 20 can also be controlled using control data generated as set out in method S300 (illustrated in FIG. 17). The control data can be generated according to a protocol as set out in method S400 (as illustrated in FIG. 18).

FIGS. 30 and 31 illustrate an upper body support system 500. The support system 500 may be part of a wheelchair or it may be separate unit that can be fitted to a wheelchair. If the upper body support system 500 is a separate unit it can be transported so that a user can use the same upper body support system 500 in a variety of situations. For example, the user can use the upper body support system 500 when using transport such as a car, bus, train or aeroplane. In this case the upper body support system 500 can be used in conjunction with an existing passenger seat. The upper body support system 500 can also be used in conjunction with conventional chairs in various environments such as in the home (e.g. armchairs or dining room chairs), restaurants, offices and entertainment venues (e.g. theatres, cinemas and sports stadia). Since the upper body support system 500 can be used with conventional chairs, as well as with wheelchairs, the user's situation can be normalised. Importantly, the user can be at the same level as other people in a particular environment and there is no longer the need for the user to be in a separate area as may happen if they were seated in a wheelchair. This helps with socialisation and prevents the user feeling isolated or being treated differently to people who do not need to have their bodies supported.

The upper body support system 500 includes a back portion 502 and two side portions 504. A left side portion 504 can support the left side of a user and a right side portion 504 can be used to support the left side of a user. The upper body support system 500 may comprise only a single side portion 504 if the user tends to lean or slump to only one side.

In the example illustrated, the back portion 502 has a posterior section and two wings that extend from the posterior section in an anterior direction. In other examples (not illustrated) the wings are absent.

The side portions 504 can pivot between a deployed position, as illustrated in FIG. 30, and a stowed position, as illustrated in FIG. 31. The pivoting action may be provided by one or more hinges 506. In the particular example illustrated in FIGS. 30-32, the hinges 506 are flat edged and stop at a position in which the side portions 504 are generally parallel to the plane of the back portion 502 (this plane is illustrated as element 511 in FIG. 30). Of course, hinges of various shapes and configuration may be used according to ascetic, design and functionality considerations. In use, the plane of the back portion 502 is generally parallel to the coronal plane of the user but may vary from this according to the particular anatomy of the user (for example due to abnormal curvature of the user's spine or the user slumping)

In the deployed position the side portion(s) 504 extend generally forward (i.e. in the anterior direction) from the back portion 502, that is, generally 90 degrees from the plane of the back portion 502. That is, the side portion(s) 504 are open. The deployed position corresponds to a position of the side portions 504 when a user is using the upper body support system 500 to support herself. The side portion(s) 504 may be inclined at different positions relative to the 90 degree position according to the support needs of the user, e.g. in the range +/−45 degrees from the 90 degree position.

In the stowed position the side portion(s) 504 face inwards, for example they can be generally parallel to the plane of the back portion 502 as is illustrated in FIG. 31. That is, the side portion(s) 504 are closed. In the stowed position the upper body support system 500 takes up less space. This makes the upper body support system 500 easier to transport and store.

The side portions 504 may also be placed in an "access" position (not illustrated) in which the side portions 504 are opened wider than they are in the deployed position. In the access position it is easier for a user to enter and exit the upper body support system 500. Additionally, the access position may be used when the upper body support system 500 is occupied by a user so as to provide easier access to the body of the user. For example, access may be needed to the clothing of a user or to attend to a gastrostomy feeding tube (such as a percutaneous endoscopic gastrostomy (PEG) tube).

The side portions 504 may be configured to be interchangeable. That is, a side portion 504 that is fitted to a left-hand side of the back portion 502 may be detached and fitted to the right-hand side of the back portion 502 and vice versa.

The back portion 502 and side portion(s) 504 are generally made of a rigid material so that the weight of the user can be adequately supported. As illustrated in FIG. 32, the upper body support system 500 may also have an interior back portion 552 and/or interior side portions 554 that are made of a more compliant material. For example the interior back portion 552 and/or interior side portions 554 may be made of foam (e.g. shape memory foam). The interior back portion 552 and/or interior side portions 554 may be laser cut.

The back portion 502 and side portion(s) 504 may be generic (e.g., mass produced) or they may be customised for a particular user. Similarly, the interior back portion 552 and/or interior side portions 554 may be generic or they may be customised. To save on manufacturing costs, whilst still providing a customised fit, the back portion 502 and side portion(s) 504 may be generic whilst the interior back portion 552 and/or interior side portions 554 are customised. Further customisation of the fit and level of support provided can be achieved by using the expandable body/bladder system 100 as described hereinabove. Alternatively the interior back portion 552 and/or interior side portions 554 can be replaced by the expandable body/bladder system 100.

Figure 33:
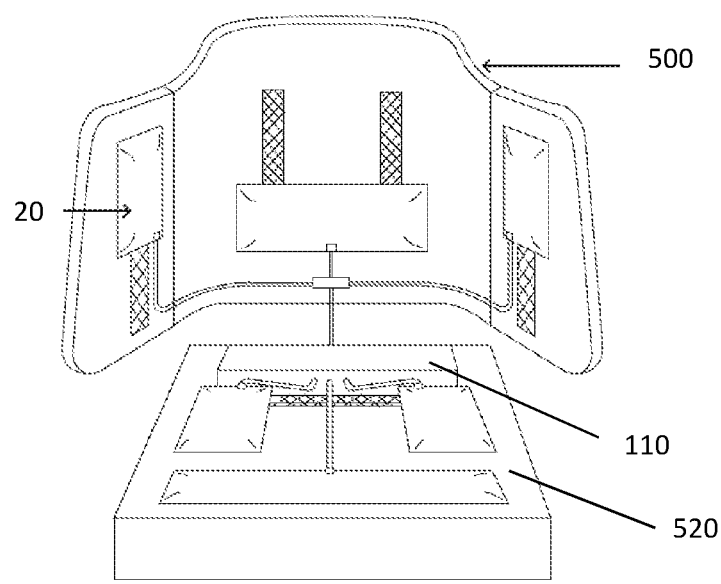
FIG. 33 illustrates the support system of FIG. 30 fitted, for example, with the bladder system of FIG. 11.

FIG. 33 illustrates an upper body support system 500 to which bladders 20 have been attached. The bladders 20 may be attached to the upper body support system 500 in the way as has been described hereinabove, for example, as described in relation to FIG. 12.

The bladders 20 are connected to the same pump 60 which may be housed in a base unit 110. As such, the system illustrated in FIG. 33 may be referred to as a "connected system". The bladders 20 and base unit 110 may take the form as previously described in relation to FIG. 11. FIG. 33 also illustrates a seat support 520 that may or may not be used in conjunction with the upper body support system 500. The base unit 110 is illustrated as being attached/supported by the seat support 520, however, it may be attached/supported anywhere that is convenient. For example, the base unit 110 may be attached/supported on a wheelchair, or other support appliance, to which the upper body support system 500 is fitted to or forms part of.

Figure 34:
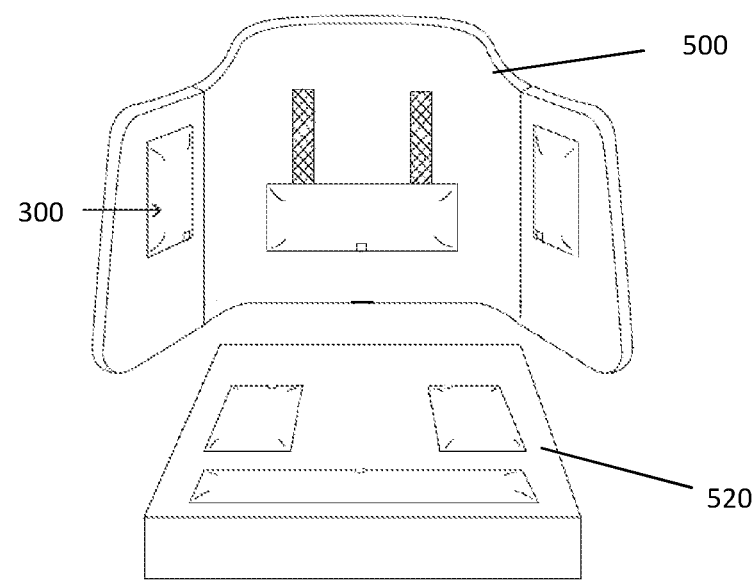
FIG. 34 illustrates the support system of FIG. 30 fitted with a modular expandable body/bladder system.

FIG. 34 illustrates an upper body support system 500 to which modules 300 have been attached. As such, the illustrated system may be referred to as a "modular system". The modules 300 may be attached to the upper body support system 500 in the same way as has been previously described for the attachment of bladders 20.

The modules 300 may be the first example modules illustrated in FIG. 28 or the second example module illustrated in FIG. 29. FIG. 33 also illustrates a seat support 520 that may or may not be used in conjunction with the upper body support system 500. Since there are no conduits or wiring between the modules 300 and a pump or (base unit) there is nothing to hinder the pivotal movement of the side portions 504 of the upper body support system 500. In particular, there is no danger of a wires or conduits being trapped or damaged between the side portions 504 and the back portion 502.

The upper body support system 500 may be folded into a stowed position whilst leaving in place the bladders 20 or modules 300. However, such folding may be easier when the modular system is used. For both the connected system and the modular system, if a seat support 520 is used it can be transported or stored separately. Such transportation or storage is facilitated when a modular system is used since no disconnection of conduits is required.

Since the bladders 20 or modules 300 can be placed at positions that are customised to a user, and the supports 500/520 are readily portable, the user has to opportunity to have a customised support system in a variety of situations (such as for example, armchairs or dining room chairs, and chairs in restaurants, offices and entertainment venues, e.g. theatres, cinemas and sports stadia). A particular configuration for the degree of expansion used for the bladders 20 (or other expandable bodies) may have been found to be suitable for an individual user. This configuration may be stored, for example in the controller 320 or other device that has a memory. The bladders/expandable bodies 20 may then be expanded to the required configuration when the supports 500/520 are deployed in a particular situation. The configuration may then be adjusted (i.e., "tweaked") to suit the particular situation as necessary. Various pre-set configurations may also be stored according to particular deployment situations. For example, there may be different pre-set configurations according to whether the supports 500/520 are deployed on an armchair or deployed on a dinning chair.

What is claimed is:

1. A posture support system for a person supporting appliance, the system comprising:
   a first module and a second module, each of the modules comprising:
      an expandable body,
      means for changing a degree of expansion of the expandable body;
      a sensor configured to produce measurement data corresponding to the degree of expansion of the expandable body;

a processor arranged to process the measurement data generated from the sensor; and a wireless communication unit arranged to transmit the measurement data wirelessly to a controller and receive control data to control the degree of expansion of the expandable body, said controller comprising one or more of: (I) a mobile telephone; (ii) a laptop computer; (iii) a PC; (iv) a mainframe computer;

wherein the wireless communication unit of the first module is configured to communicate wirelessly to the communication unit of the second module such that the expandable body of the first module is configured to change a distance with the expandable body of the second module in response to a signal from the wireless communication unit of the second module.

2. The system of claim 1, comprising a container for containing at least the expandable body and the means for changing the degree of expansion of at least one of the expandable bodies, wherein the container also contains at least one of the following: (i) the sensor; (ii) the processor; (iii) the wireless communication unit; or (iv) any combination of (i)-(iii).

3. The system of claim 1, comprising means to connect the module to the person supporting appliance.

4. The system of claim 1, wherein the system comprises the controller.

5. The system of claim 1, wherein at least one of the expandable bodies is an inflatable bladder and the means for changing the degree of expansion of the inflatable bladder is a source of compressed gas.

6. The system of claim 1, comprising a shape memory component covering a surface of at least one of the expandable bodies.

7. The system of claim 1, comprising a rigid structure to which at least one of the modules is attached or are adapted to be attached, wherein the rigid structure comprises:

a back support portion comprising at least one lateral support portion connected to, and extending from, a lateral side of the back support portion.

8. A posture support assembly for a person supporting appliance, the assembly comprising:

an attachment surface;

at least two expandable bodies having an attachment arranged to attach to the attachment surface at a position that has two degrees of freedom on the attachment surface, each expandable body coupled to a separate wireless communication unit; and a shape memory material arranged to: (i) fit over at least one of the expandable bodies when the at least one expandable body is attached to the attachment surface, and/or (ii) be coupled to at least one of the expandable bodies and wherein the attachment surface is a surface of a component of the person supporting appliance that provides support to the person of a user of the person supporting appliance and wherein the shape memory material comprises viscoelastic polyurethane foam and a rigid structure to which the expandable bodies are attached or are adapted to be attached;

wherein at least one of the expandable bodies is configured to change a distance between at least two of the expandable bodies in response to a wireless signal from the wireless communication unit of another of the at least two expandable bodies indicating changing a degree of expansion of the another expandable body of the at least two expandable bodies.

9. The posture support assembly of claim 8, wherein the attachment surface and the attachment together form a hook and loop attachment system.

10. The system of claim 7, further comprising:

a cover configured to fit over a component of a person supporting appliance, the component having a posture support assembly, the posture support assembly comprising an expandable body, wherein, the cover is configured to fit over the component when the expandable body is in an unexpanded/stowed state and remain fitted to the component when the expandable body is in an expanded; deployed form and wherein the component is a back support, a head support, a thoracic support, a neck support, a lumbar support, a foot support, or a pommel designed to fit between the legs of a user, and wherein the cover has one or more elasticated perimeter portions configured to engage the component when the expandable body is in the unexpanded/stowed state and/or one or more access openings, such as a slit, that provide a user access at least one of the expandable bodies of the posture support system.

11. The system of claim 10, further comprising a person supporting appliance.

12. The system of claim 10, further comprising a set of instructions, wherein the set of instructions comprises instructions to: fit the cover to the component when at least one of the expandable bodies is in stowed state; and expanding the at least one of the expandable bodies.

13. A method of adjusting a person supporting appliance, the method comprising the steps:

(a) providing a support surface having an outward facing attachment surface;

(b) placing at least two expandable bodies at a chosen positions on the attachment surface; and (c) providing a first control signal to a first wireless communication unit to after a degree of expansion of one of the at least two expandable bodies to change a distance between the at least two expandable bodies and wirelessly transmitting a second control signal to a second wireless communication unit to alter a degree of expansion of another of the at least two expandable bodies; and (d) fitting a cover to a person supporting appliance component, the person supporting appliance component having the attachment surface with at least one of the expandable bodies attached thereto, wherein the cover has an aperture that has dimensions that allow access for a person's fingers so that the person may place the at least one of the expandable bodies at chosen positions on the attachment surface, wherein step (c) occurs before step (b) and/or wherein step (d) occurs before step (c), and the method also comprising moving the at least one of the at least two expandable bodies to a different position on the attachment surface.

* * * * *